(12) United States Patent
Walters et al.

(10) Patent No.: US 10,064,863 B2
(45) Date of Patent: Sep. 4, 2018

(54) FORMULATIONS OF 3-(5-AMINO-2-METHYL-4-OXO-4H-QUINAZOLIN-3-YL)-PIPERIDINE-2,6-DIONE

(71) Applicant: Celgene Corporation, Summit, NJ (US)

(72) Inventors: Colin Walters, Monroe Township, NJ (US); William Bowen, Madison, NJ (US); Yali Sun, Livingtston, NJ (US); Jay Brumfield, Westfield, NJ (US); Xiaoxuan Shen, Livingston, NJ (US); Daozhong Zou, Raritan, NJ (US); Indrajit Ghosh, Hillsborough, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 15/249,082

(22) Filed: Aug. 26, 2016

(65) Prior Publication Data

US 2017/0056323 A1   Mar. 2, 2017

Related U.S. Application Data

(60) Provisional application No. 62/210,923, filed on Aug. 27, 2015.

(51) Int. Cl.
*A61K 31/517* (2006.01)
*A61K 9/48* (2006.01)

(52) U.S. Cl.
CPC .......... *A61K 31/517* (2013.01); *A61K 9/4858* (2013.01); *A61K 9/4866* (2013.01)

(58) Field of Classification Search
CPC .................................................. A61K 31/517
See application file for complete search history.

(56) References Cited

U.S. PATENT DOCUMENTS

| 7,635,700 B2 | 12/2009 | Muller et al. |
| 2015/0126538 A1 | 5/2015 | Muller et al. |
| 2015/0196562 A1 | 7/2015 | Bhat |

OTHER PUBLICATIONS

Aljaberi et al. (Drug Development and Industrial Pharmacy, 2009;35(9):1066-1071).*
Hagner et al., "CC-122, a pleitropic pathway modifier, mimics an interferon response and has antitumor activity in DLBCL," *Blood*, 126(6):779-789 (2015).
John et al., "Formulating weakly basic HCI salts: relative ability of common excipients to induce disporportionation and the unique deleterious effects of magnesium stearate," *Pharm. Res.*, 30:1628-1641 (2013).

* cited by examiner

*Primary Examiner* — Benjamin Packard
(74) *Attorney, Agent, or Firm* — Jones Day

(57) ABSTRACT

Pharmaceutical compositions and single unit dosage forms of Compound A (3-(5-amino-2-methyl-4-oxo-4H-quinazolin-3-yl)-piperidine-2,6-dione), or an enantiomer or a mixture of enantiomers thereof, a pharmaceutically acceptable salt, solvate, hydrate, co-crystal, clathrate, or polymorph thereof, are provided herein. Also provided are methods of treating, managing, or preventing cancer using the dosage forms described herein.

21 Claims, 6 Drawing Sheets

Figure 1:
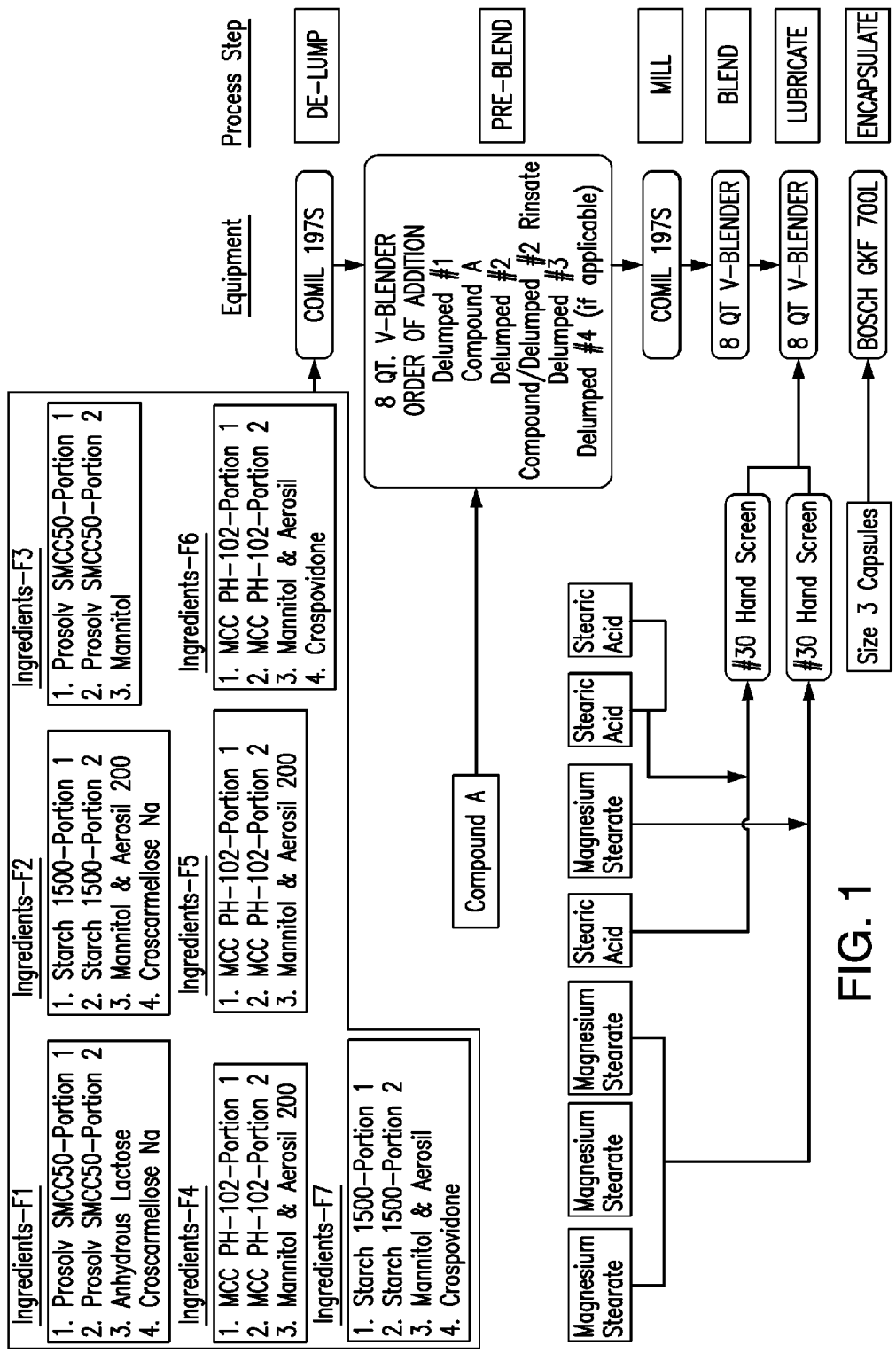

FORMULATIONS OF 3-(5-AMINO-2-METHYL-4-OXO-4H-QUINAZOLIN-3-YL)-PIPERIDINE-2,6-DIONE

This application claims priority to U.S. Provisional Application No. 62/210,923, filed Aug. 27, 2015, the entirety of which is incorporated herein by reference.

1. FIELD

Provided herein are formulations and dosage forms of 3-(5-amino-2-methyl-4-oxo-4H-quinazolin-3-yl)-piperidine-2,6-dione. Methods of using the formulations and dosage forms for treating, managing, or preventing cancer are also provided herein.

2. BACKGROUND

Drug substances are usually administered as part of a formulation in combination with one or more other agents that serve varied and specialized pharmaceutical functions. Dosage forms of various types may be made through selective use of pharmaceutical excipients. Pharmaceutical excipients have various functions and contribute to the pharmaceutical formulations in many different ways, e.g., solubilization, dilution, thickening, stabilization, preservation, coloring, flavoring, etc. The properties of pharmaceutical excipients that are considered when formulating an active drug substance include bioavailability, ease of manufacture, ease of administration, and stability of the dosage form. Due to the varying properties of the active drug substance to be formulated, and cross-reactivity between excipients, dosage forms typically require pharmaceutical excipients that are uniquely tailored to the active drug substance to achieve advantageous physical and pharmaceutical properties.

Nevertheless, use of pharmaceutical excipients in formulating dosage forms can, in some instances, cause undesirable adverse reactions with the active ingredient which manifest upon, for example, prolonged storage or contact with water. Indeed, it is well known that the properties of the final dosage form (e.g, its bioavailability and stability) are, for the most part, highly dependent on the excipients chosen, their concentration and interaction with both the active compound and each other. Excipients are more than inert or inactive ingredients and must be selected to avoid undesirable cross-reaction with active ingredients and other excipients in the formulation. Selecting compatible excipients is critical in formulating dosage forms to ensure the active ingredient is properly delivered and that the dosage form is a stable formulation.

Thus, there is a need in the art for formulations of Compound A in combination with pharmaceutical excipients which reduce or eliminate undesirable reactivity of pharmaceutical excipients with Compound A in the formulation. Provided herein are solutions to these and other problems in the art by providing dosage forms which provide stable formulations of Compound A lacking both undesirable interactions (e.g., incompatibilities) between Compound A and the excipients of the formulated dosage form and undesirable interactions between excipients.

3. BRIEF SUMMARY

Provided herein are dosage forms containing Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof which reduce or eliminate reactivity of pharmaceutical excipients, including lubricants, disintegrants, and fillers or binders, with the active ingredient (e.g., Compound A). Reactivity of Compound A with lubricants, disintegrants, or fillers or binders can decrease the formulation stability and thereby reduce or eliminate the therapeutic value of Compound A in the formulation. The formulations provided herein provide stable formulations of Compound A with no incompatibility problems between agents in the in formulation. In one embodiment, the dosage form is an oral dosage form. In one embodiment, the oral dosage form is in the form of a capsule.

In one aspect is an oral dosage form in the form of a capsule which includes Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount of about 0.5 to about 5 weight percent of the total weight of the composition; a binder or filler at an amount of about 90 to 98 weight percent of total weight of the composition, and a lubricant, where the binder or filler is not lactose.

In another aspect is an oral dosage form which weighs about 100 mg and includes: Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 0.5 mg Compound A; and a pharmaceutically acceptable carrier or excipient that includes a lubricant.

In another aspect is an oral dosage form which weighs about 100 mg and includes: Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 1 mg Compound A; and a pharmaceutically acceptable carrier or excipient that includes a lubricant.

In yet another aspect is an oral dosage form which weighs about 120 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 3 mg Compound A and a pharmaceutically acceptable carrier or excipient that includes a lubricant.

In still another aspect is an oral dosage form that weighs about 200 mg and includes: Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 2 mg Compound A and a pharmaceutically acceptable carrier or excipient that includes a lubricant.

In another aspect is an oral dosage form which weighs about 140 mg and includes: Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 3.5 mg Compound A; and a pharmaceutically acceptable carrier or excipient that includes a lubricant.

In another aspect is an oral dosage form which weighs about 160 mg and includes: Compound A (3-(5-amino-2-methyl-4-oxo-4H-quinazolin-3-yl)-piperidine-2,6-dione), or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 4 mg Compound A; and a pharmaceutically acceptable carrier or excipient that includes a lubricant.

In yet another aspect is an oral dosage form that weighs about 200 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 5 mg Compound A and a pharmaceutically acceptable carrier or excipient that includes a lubricant.

In still another aspect is an oral dosage form that includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 0.5, 1, 2, 3, 3.5, 4, or 5 mg Compound A and a pharmaceutically acceptable carrier or excipient that includes a lubricant.

In one embodiment, the dosage forms provided herein comprises the HCl salt of Compound A.

In another aspect are methods of treating, managing, ameliorating or preventing cancer, including primary and metastatic cancer, as well as cancer that is refractory or resistant to conventional chemotherapy (e.g., lymphoma, multiple myeloma, leukemia, and solid tumors) by administering to a patient in need of such treatment or prevention a therapeutically or prophylactically effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form as described herein.

In another aspect are oral dosage forms for use in a method of treating, managing, ameliorating or preventing cancer, including primary and metastatic cancer, as well as cancer that is refractory or resistant to conventional chemotherapy (e.g., lymphoma, multiple myeloma, leukemia, and solid tumors) by administering to a patient in need of such treatment or prevention a therapeutically or prophylactically effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form as described herein.

Lymphomas treated, managed, ameliorated, or prevented by the methods described herein include, for example, Hodgkin's lymphoma, non-Hodgkin's lymphoma, AIDS-related lymphomas, anaplastic large-cell lymphoma, angioimmunoblastic lymphoma, blastic NK-cell lymphoma, Burkitt's lymphoma, Burkitt-like lymphoma (small non-cleaved cell lymphoma, small lymphocytic lymphoma, cutaneous T-cell lymphoma, diffuse large B-cell Lymphoma, enteropathy-type T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas or Waldenstrom's macroglobulinemia.

In another aspect is a method of treating, managing, ameliorating or preventing acute myeloid leukemia (AML), T-cell leukemia, chronic myeloid leukemia (CML), chronic lymphocytic leukemia (CLL) and acute lymphoblastic leukemia (ALL).

In another aspect is an oral dosage form for use in a method of treating, managing, ameliorating or preventing acute myeloid leukemia (AML), T-cell leukemia, chronic myeloid leukemia (CML), chronic lymphocytic leukemia (CLL) and acute lymphoblastic leukemia (ALL).

In another aspect is a method of treating, managing, ameliorating or preventing melanoma, head and neck tumors, breast carcinoma, non-small cell lung carcinoma, ovarian carcinoma, pancreatic carcinoma, prostate carcinoma, colorectal carcinoma, and hepatocellular carcinoma.

In another aspect is an oral dosage form for use in a method of treating, managing, ameliorating or preventing melanoma, head and neck tumors, breast carcinoma, non-small cell lung carcinoma, ovarian carcinoma, pancreatic carcinoma, prostate carcinoma, colorectal carcinoma, and hepatocellular carcinoma.

Cancers that can be treated, managed, ameliorated, or prevented by the methods described herein include for example, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, or leiomyoma.

4. BRIEF DESCRIPTION OF THE DRAWINGS

FIG. 1. Illustrates a process flow diagram for synthesizing batches of Compound A.

Figure 2A:
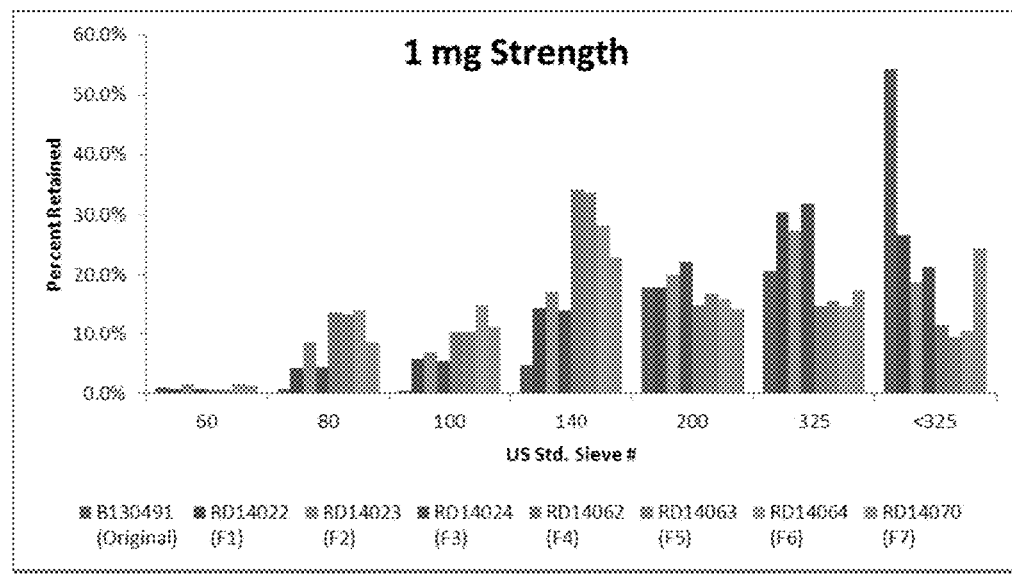

FIG. 2A. Illustrates particle size distribution for 1 mg strength Compound A.

Figure 2B:
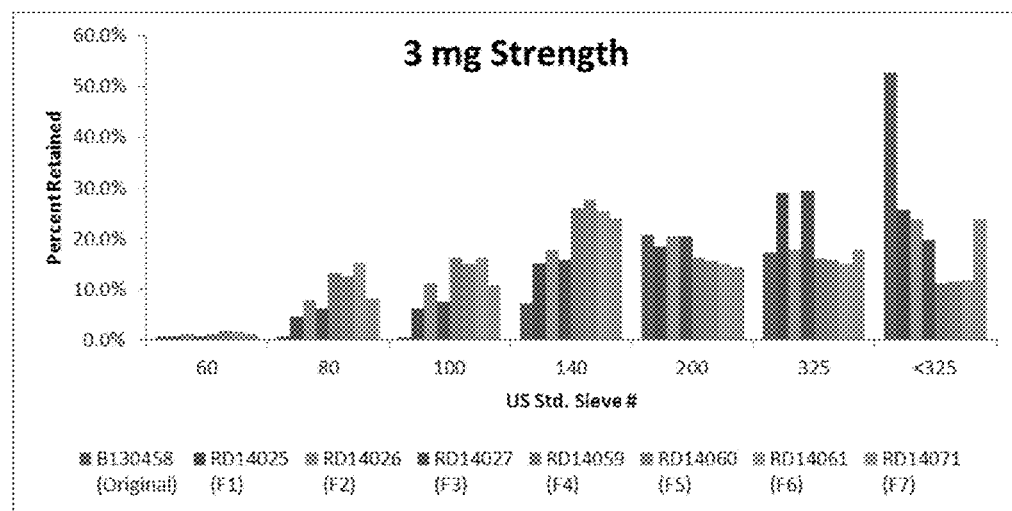

FIG. 2B. Illustrates particle size distribution for 3 mg strength Compound A.

Figure 3A:
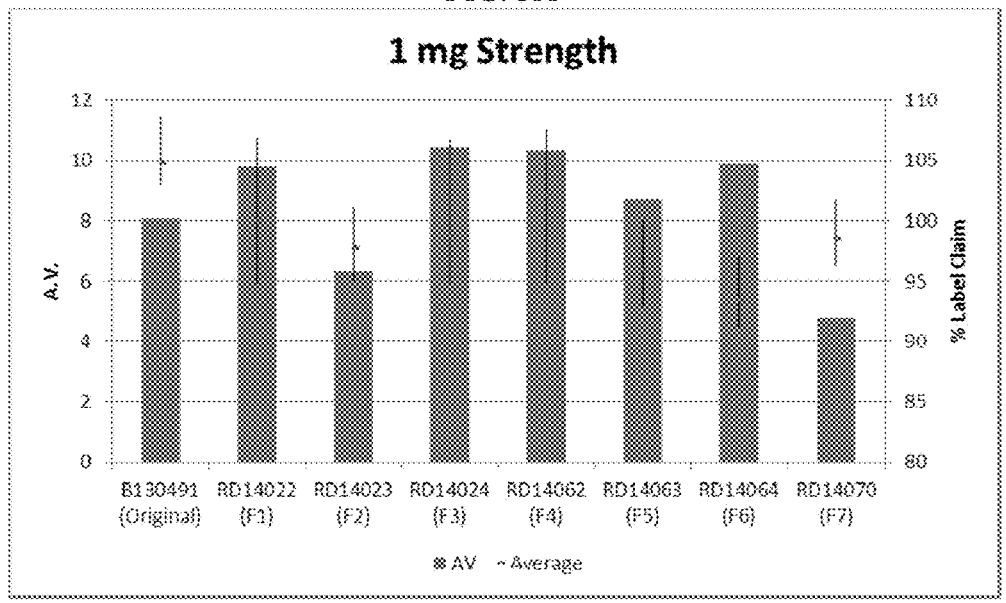

FIG. 3A. Illustrates bulk product content uniformity test results for the control and test formulations for 1 mg strength Compound A.

Figure 3B:
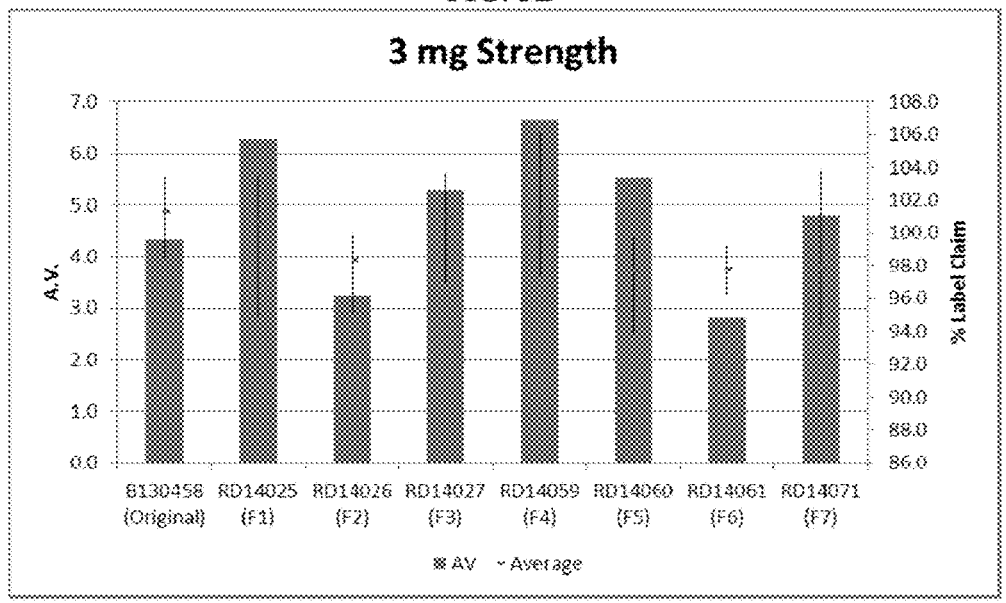

FIG. 3B. Illustrates bulk product content uniformity test results for the control and test formulations for 3 mg strength Compound A.

Figure 4A:
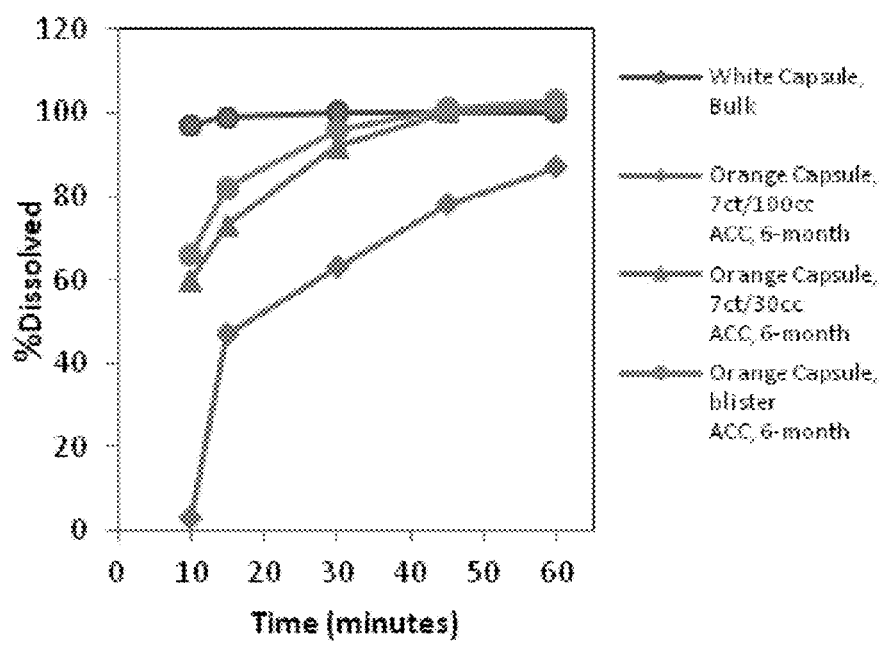

FIG. 4A. Illustrates the dissolution profile of Compound A formulations containing lactose, croscarmellose sodium, and magnesium stearate in 1 mg capsule of Compound A.

Figure 4B:
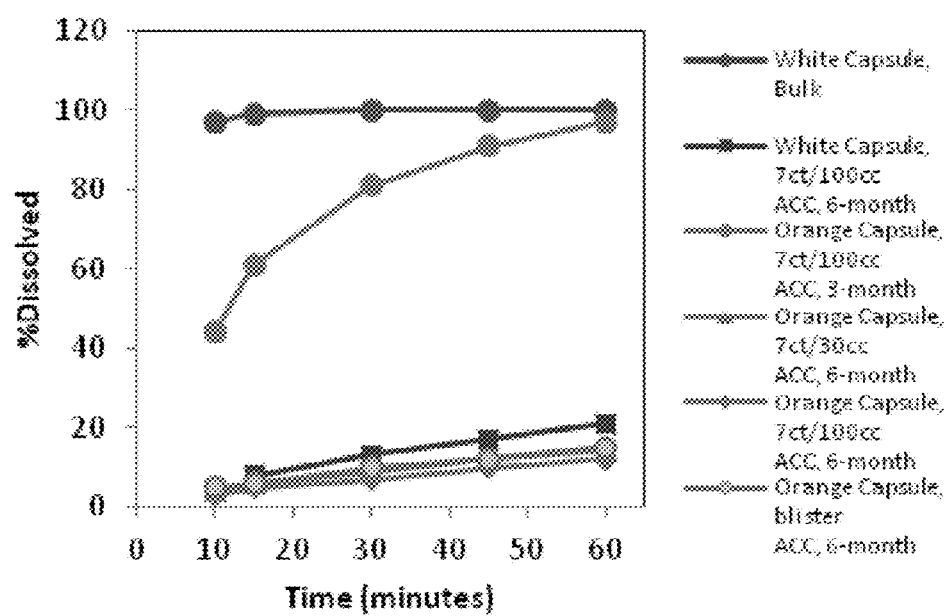

FIG. 4B. Illustrates the dissolution profile of Compound A formulations containing lactose, croscarmellose sodium, and magnesium stearate in 3 mg capsule of Compound A.

Figure 5A:
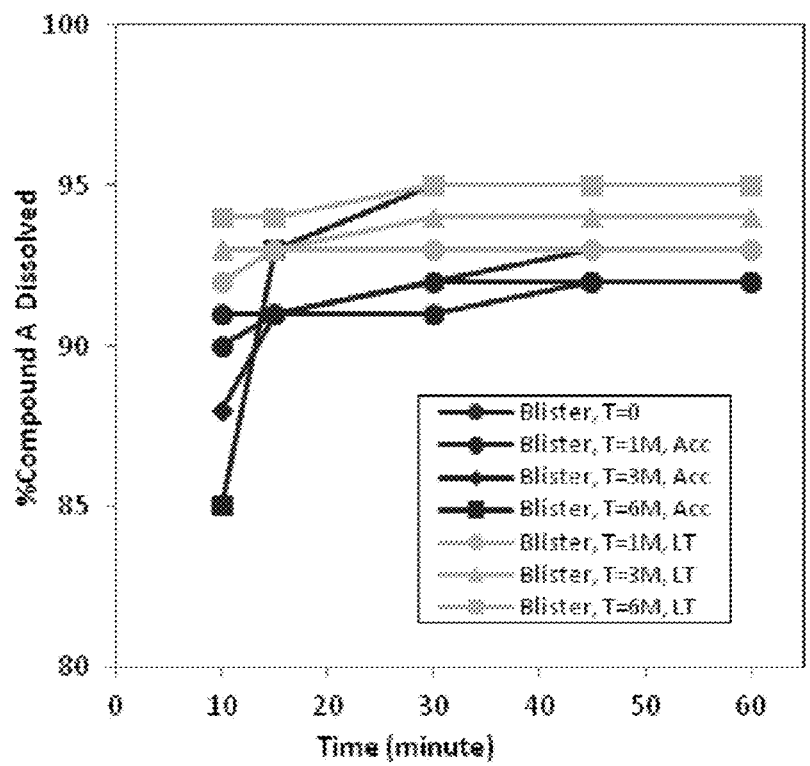

FIG. 5A. Illustrates the dissolution profile of Compound A formulation that does not contain lactose, croscarmellose sodium or magnesium stearate in a 1 mg capsule of Compound A (Formulation F6) from blister packs.

Figure 5B:
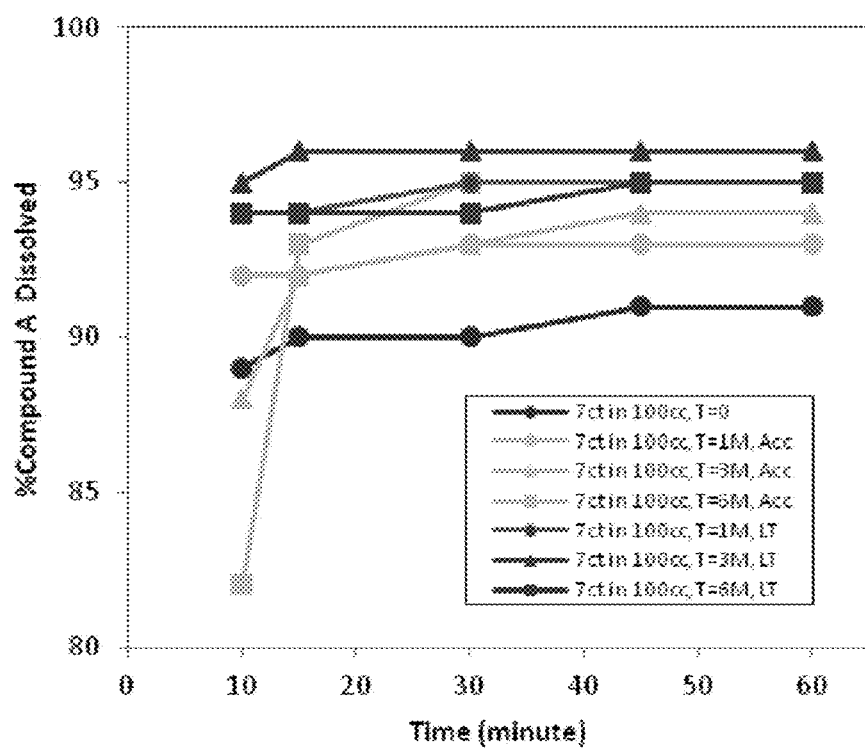

FIG. 5B. Illustrates the dissolution profile of Compound A formulation that does not contain lactose, croscarmellose sodium or magnesium stearate in a 1 mg capsule of Compound A (Formulation F6) stored in a bottle.

Figure 6A:
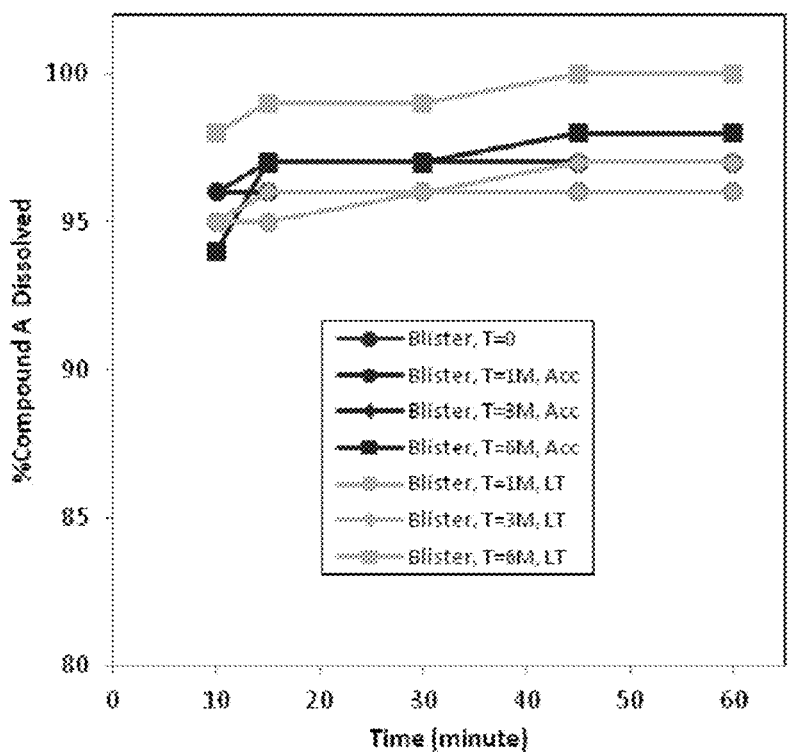

FIG. 6A. Illustrates the dissolution profile of Compound A formulation that does not contain lactose, croscarmellose sodium or magnesium stearate in a 3 mg capsule of Compound A (Formulation F6) from blister packs.

Figure 6B:
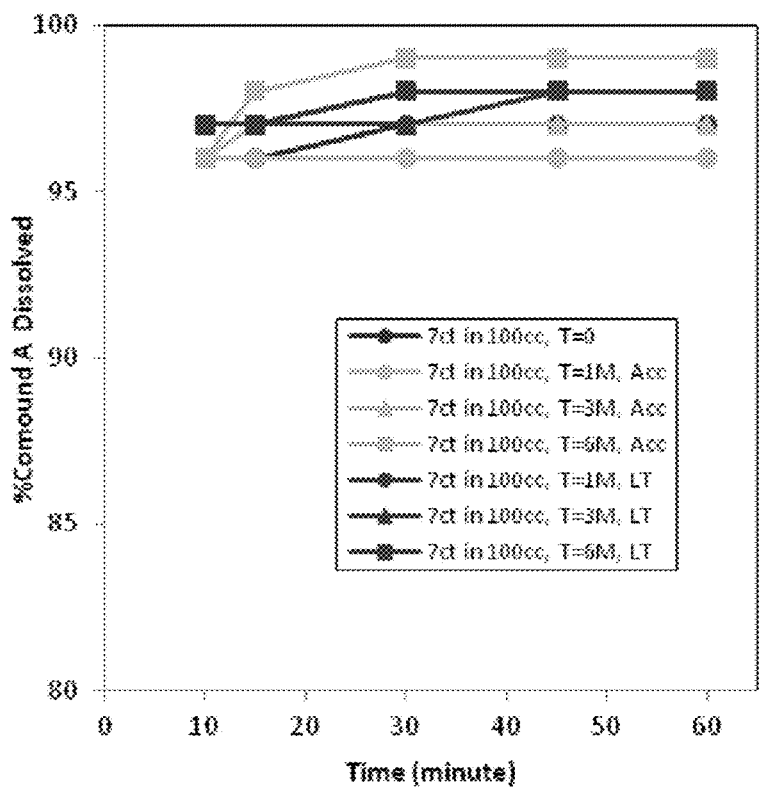

FIG. 6B. Illustrates the dissolution profile of Compound A formulation that does not contain lactose, croscarmellose sodium or magnesium stearate in a 3 mg capsule of Compound A (Formulation F6) stored in a bottle.

5. DETAILED DESCRIPTION

5.1 Definitions

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The terms "3-(5-amino-2-methyl-4-oxo-4H-quinazolin-3-yl)-piperidine-2,6-dione" and "Compound A" refer to a compound having structure:

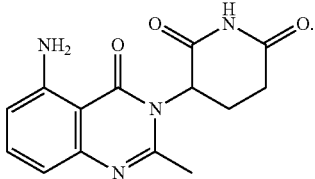 [SMILES: Cc1nc2cccc(N)c2c(=O)n1C1CCC(=O)NC1=O]

Compound A also refers to enantiomers or a mixture of enantiomers thereof, pharmaceutically acceptable stereoisomers, pharmaceutically acceptable salts, prodrugs, solvates, hydrates, co-crystals, clathrates, or polymorphs thereof. In embodiments, Compound A refers to the base and pharmaceutically acceptable salts thereof.

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein, unless otherwise specified, the term "pharmaceutically acceptable salt(s)," as used herein includes, but is not limited to, salts of acidic or basic moieties of compounds described herein (e.g., Compound A). Basic moieties are capable of forming a wide variety of salts with various inorganic and organic acids. The acids that can be used to prepare pharmaceutically acceptable acid addition salts of such basic compounds are those that form non-toxic acid addition salts, e.g., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (e.g., 1,1'-methylene-bis-(2-hydroxy-3-naphthoate) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "prodrug" means a derivative of a compound that can hydrolyze, oxidize, or otherwise react under biological conditions (in-vitro or in-vivo) to provide the compound. Examples of prodrugs include, but are not limited to, derivatives of compounds described herein (e.g., Compound A) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein (e.g., Compound A) that include NO, $NO_2$, ONO, or $ONO_2$ moieties.

As used herein and unless otherwise indicated, the terms "biohydrolyzable carbamate," "biohydrolyzable carbonate," "biohydrolyzable ureide," "biohydrolyzable phosphate" refer to a carbamate, carbonate, ureide, or phosphate, respectively, of a compound that either: 1) does not interfere with the biological activity of the compound, but can confer upon that compound advantageous properties in-vivo, such as uptake, duration of action, or onset of action; or 2) is biologically inactive but is converted in-vivo to the biologically active compound. Examples of biohydrolyzable carbamates include, for example, lower alkylamines, substituted ethylenediamines, amino acids, hydroxyalkylamines, heterocyclic and heteroaromatic amines, and polyether amines.

As used herein and unless otherwise indicated, the term "biohydrolyzable ester" refers to an ester of a compound that either: 1) does not interfere with the biological activity of the compound, but can confer upon that compound advantageous properties in-vivo, such as uptake, duration of action, or onset of action; or 2) is biologically inactive but is converted in-vivo to the biologically active compound. Examples of biohydrolyzable esters include, but are not limited to, lower alkyl esters, alkoxyacyloxy esters, alkyl acylamino alkyl esters, and choline esters.

As used herein and unless otherwise indicated, the term "biohydrolyzable amide" means an amide of a compound that either: 1) does not interfere with the biological activity of the compound, but can confer upon that compound advantageous properties in-vivo, such as uptake, duration of action, or onset of action; or 2) is biologically inactive but is converted in-vivo to the biologically active compound. Examples of biohydrolyzable amides include, but are not limited to, lower alkyl amides, α amino acid amides, alkoxyacyl amides, and alkylaminoalkylcarbonyl amides.

A "pharmaceutically acceptable excipient," refers to a substance that aids the administration of an active agent to a subject by for example modifying the stability of an active agent or modifying the absorption by a subject upon administration. A pharmaceutically acceptable excipient typically has no significant adverse toxicological effect on the patient. Examples of pharmaceutically acceptable excipients include, for example, water, NaCl (including salt solutions), normal saline solutions, sucrose, glucose, binders, fillers, disintegrants, lubricants, coatings, sweeteners, flavors, alcohols, oils, gelatins, carbohydrates such as amylose or starch, fatty acid esters, hydroxymethycellulose, polyvinyl pyrrolidine, and colors, and the like. One of skill in the art will recognize that other pharmaceutical excipients known in the art are useful in the present invention and include those listed in for example the *Handbook of Pharmaceutical Excipients*, Rowe R. C., Shesky P. J., and Quinn M. E., 6$^{th}$ Ed., The Pharmaceutical Press, RPS Publishing (2009). The terms "binder," "filler," "disintegrant," and "lubricant" are used in accordance with the plain and ordinary meaning within the art.

In certain embodiments, a pharmaceutically acceptable excipient may be incompatible (e.g., cross-reacts) with other excipients or active agents described herein. In some embodiments, magnesium stearate, croscarmellose sodium, lactose, excipients comprising Mg, Ca, K, Li, or Nucleic acid, acesulfame potassium, ammonium alginate, calcium acetate, calcium alginate, calcium carbonate, calcium chloride, calcium lactate, calcium phosphate, calcium silicate, calcium stearate, calcium sulfate, carboxymethylcellulose calcium, carboxymethylcellulose sodium, docusate sodium, glycine, kaolin, magnesium aluminum silicate, magnesium carbonate, magnesium oxide, magnesium silicate, magnesium trisilicate, polacrilin potassium, polymethacrylates, postassium alginate, postassium benzoate, potassium bicarbonate, postassium chloride, potassium citrate, sodium alginate, sodium benzoate, sodium chloride, sodium lauryl sulfate, sodium starch glycolate, sodium stearyl fumarate, sulfobutylether beta-cyclodextrin, sodium stearate, talc, or zinc stearate are incompatible in the dosage forms described herein. In one embodiment magnesium stearate, croscarmellose sodium, and lactose are incompatible in the dosage forms described herein.

In other embodiments, the pharmaceutically acceptable excipient is not selected from magnesium stearate, croscarmellose sodium, lactose, excipients comprising Mg, Ca, K, Li, or Na, acesulfame potassium, ammonium alginate, calcium acetate, calcium alginate, calcium carbonate, calcium chloride, calcium lactate, calcium phosphate, calcium silicate, calcium stearate, calcium sulfate, carboxymethylcellulose calcium, carboxymethylcellulose sodium, docusate sodium, glycine, kaolin, magnesium aluminum silicate, magnesium carbonate, magnesium oxide, magnesium silicate, magnesium trisilicate, polacrilin potassium, polymethacrylates, postassium alginate, postassium benzoate, potassium bicarbonate, postassium chloride, potassium citrate, sodium alginate, sodium benzoate, sodium chloride, sodium lauryl sulfate, sodium starch glycolate, sodium stearyl fumarate, sulfobutylether beta-cyclodextrin, sodium stearate, talc, or zinc stearate (e.g., the dosage forms described herein do not include one or more of the above-recited pharmaceutically acceptable excipients. In one embodiment, the pharmaceutically acceptable excipient is not magnesium stearate, croscarmellose sodium, and lactose. Thus in certain instances, dosage forms described herein can exclude one or more of magnesium stearate, croscarmellose sodium, and lactose.

As used herein, "administer" or "administration" refers to the act of physically delivering a substance as it exists outside the body into a subject. Administration includes all forms known in the art for delivering therapeutic agents, including but not limited to oral, topical, mucosal, injections, intradermal, intravenous, intramuscular delivery or other method of physical delivery described herein or known in the art (e.g., implantation of a slow-release device, such as a mini-osmotic pump to a subject; liposomal formulations; buccal; sublingual; palatal; gingival; nasal; vaginal; rectal; intra-arteriole; intraperitoneal; intraventricular; intracranial; or transdermal). Preferably, the compositions described herein are administered orally (e.g., by capsule or tablet).

By "co-administer" it is meant that a composition described herein is administered at the same time, just prior to, or just after the administration of one or more additional therapeutic compositions, including for example an anti-cancer agent. Co-administration is meant to include simultaneous or sequential administration of compound individually or in combination (more than one compound or agent). Co-administration includes administering two active agents simultaneously, approximately simultaneously (e.g., within about 1, 5, 10, 15, 20, or 30 minutes of each other), or sequentially in any order. Thus, co-administration can include administering one active agent (e.g. a compound described herein) within 0.5, 1, 2, 4, 6, 8, 10, 12, 16, 20, or 24 hours of a second active agent. Co-administration can also be accomplished by co-formulation, e.g., preparing a single dosage form including both active agents. The active agents can be formulated separately. In such instances, the active agents are admixed and included together in the final form of the dosage unit. Alternatively, co-administration as described herein can include administering two separate unit dosage forms of at least two separate active agents (e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof and a second active agent described herein).

As used herein, the term "daily" is intended to mean that a therapeutic compound, such as Compound A, is administered once or more than once each day for a period of time. The term "continuous" is intended to mean that a therapeutic compound, such as Compound A, is administered daily for an uninterrupted period of at least 10 days to 52 weeks. The term "intermittent" or "intermittently" as used herein is intended to mean stopping and starting at either regular or irregular intervals. For example, intermittent administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound A, is administered daily or continuously but with a rest period.

An "effective amount" is an amount sufficient to achieve the effect for which it is administered (e.g., treat a disease or reduce one or more symptoms of a disease or condition). Thus, administration of an "amount" of a compound described herein to a subject refers to administration of "an amount effective," to achieve the desired therapeutic result. A "therapeutically effective amount" of a compound described herein for purposes herein is thus determined by such considerations as are known in the art. The term "therapeutically effective amount" of a composition described herein (e.g., 3-(5-amino-2-methyl-4-oxo-4H-quinazolin-3-yl)-piperidine-2,6-dione, or a pharmaceutically acceptable salt or solvate thereof) refers to the amount of the composition that, when administered, is sufficient to treat one or more of the symptoms of a disease described herein (e.g., lupus, cancer, or scleroderma). Administration of a compound described herein can be determined according to factors such as, for example, the disease state, age, sex, and weight of the individual. A therapeutically effective amount also refers to any toxic or detrimental effects of 3-(5-amino-2-methyl-4-oxo-4H-quinazolin-3-yl)-piperidine-2,6-dione, or a pharmaceutically acceptable salt or solvate thereof are outweighed by the therapeutically beneficial effects.

As used herein the terms "treat," "treating" and "treatment" contemplate an action that occurs while a subject is suspected, diagnosed or suffering from a disease described herein (e.g., lupus, cancer, or scleroderma), which reduces the severity or symptoms of the disease, or retards or slows the progression or symptoms of the disease.

The terms "subject," "patient," "subject in need thereof," and "patient in need thereof" are herein used interchangeably and refer to a living organism suffering from one or more of the diseases described herein (e.g., lupus, cancer, scleroderma) that can be treated by administration of a composition described herein. Non-limiting examples of organisms include humans, other mammals, bovines, rats, mice, dogs, monkeys, goat, sheep, cows, deer, and other non-mammalian animals. In embodiments, a subject is human. A human subject can be between the ages of about 1 year old to about 100 years old. In embodiments, subjects herein can be characterized by the disease being treated (e.g., a "lupus subject", a "cancer subject", or a "scleroderma subject").

As used herein, the term "plasma concentration at steady state" is the concentration reached after a period of administration of a compound provided herein, e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. Once steady state is reached, there can be minor peaks and troughs on the time dependent curve of the plasma concentration of the compound.

As used herein, and unless otherwise specified, the terms "prevent," "preventing" and "prevention" refer to the prevention of the onset, recurrence or spread of a disease or disorder, or of one or more symptoms thereof. The terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, or lengthening the time that a patient who has suffered from the disease or disorder remains in remission. The terms encompass modulating the threshold, development or duration of the disease or disorder, or changing the way that a patient responds to the disease or disorder.

As used herein, and unless otherwise specified, the term "about," when used in connection with doses, amounts, or weight percent of ingredients of a composition or a dosage form, means dose, amount, or weight percent that is recognized by those of ordinary skill in the art to provide a pharmacological effect equivalent to that obtained from the specified dose, amount, or weight percent is encompassed. Specifically, the term "about" contemplates a dose, amount, or weight percent within 30%, 25%, 20%, 15%, 10%, or 5% of the specified dose, amount, or weight percent is encompassed.

As used herein, and unless otherwise specified, the term "stable," when used in connection with a formulation or a dosage form, means that the active ingredient of the formulation or dosage form remains solubilized for a specified amount of time and does not significantly degrade or aggregate or become otherwise modified (e.g., as determined, for example, by HPLC). In some embodiments, about 70 percent or greater, about 80 percent or greater or about 90 percent or greater of the compound remains solubilized after the specified period. Stability can also refer to the compatibility of pharmaceutically acceptable excipients described herein. Accordingly, a dosage form can be considered stable when the combined pharmaceutically acceptable excipients and active agent(s) described herein do not degrade or otherwise modify (e.g., react with) the effectiveness or therapeutic value of an active agent described herein.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma

5.2 Compositions and Dosage Forms

Provided herein are dosage forms suitable for administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof to a subject (e.g., a human). In one aspect is provided an oral dosage form in the form of a capsule which includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount of about 0.5 to about 5% weight percent of the total weight of the dosage form, a binder or filler at an amount of about 90 to 98 weight percent of the total weight of the dosage form, where the binder or filler is not lactose, and a lubricant.

In one embodiment, the dosage forms provided herein comprises the HCl salt of Compound A.

The dosage forms described herein can be single unit dosages suitable for oral administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof to a human. Dosage forms described herein are stable (e.g., the compounds described herein retain activity in treating an indication after a period of time described herein). The dosage forms described herein include Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount equal to or greater than about than about 0.01, 0.02, 0.03, 0.05, 0.08 0.1, 0.2, 0.3, 0.4, 0.5, 1, 2, 3, 5, 10, 15, or 20 mg. The dosage forms further include a pharmaceutically acceptable excipient where the pharmaceutically acceptable excipient includes one or more of a filler or binder, a disintegrant, and a lubricant. In some embodiments, the amount of active ingredient is from about 0.01 to about 20 mg, from about 0.05 to about 10 mg, from about 0.08 to about 5 mg, from about 0.1 mg to about 10 mg, from about 0.1 mg to about 5 mg, or from about 1 to about 5 mg. The amount of the active ingredient can be about 0.5 mg. The amount of the active ingredient can be about 1 mg. The amount of the active ingredient can be about 2 mg. The amount of the active ingredient can be about 3 mg. The amount of the active ingredient can be about 3.5 mg. The amount of the active ingredient can be about 4 mg. The amount of the active ingredient can be about 5 mg.

The dosage forms described herein include pharmaceutical compositions and formulations that can be presented as discrete dosage forms, such as capsules (e.g., gelcaps), caplets, tablets, troches, lozenges, dispersions, and suppositories each containing a predetermined amount of an active ingredient, such as Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. The active ingredient can be a powder or in granules, a solution, or a suspension in an aqueous or non-aqueous liquid, an oil-in-water emulsion, or a water-in-oil liquid emulsion. The preferred dosage forms include tablets, caplets, and capsules.

Tablets, caplets, and capsules described herein can contain from about 50 mg to about 500 mg of the pharmaceutical composition (e.g., active ingredient and excipient(s)). Capsules can be of any size. Examples of standard sizes include #000, #00, #0, #1, #2, #3, #4, and #5. See, e.g., Remington's Pharmaceutical Sciences, page 1658-1659 (Alfonso Gennaro ed., Mack Publishing Company, Easton Pa., 18th ed., 1990), which is incorporated by reference. In some embodiments, capsules provided herein are of size #1 or larger, size #2 or larger, size #3 or larger, or size #4 or larger. In one embodiment tablets, caplets, and capsules described herein can contain from about 100 to 200 mg of pharmaceutical composition. In another embodiment tablets, caplets, and capsules described herein can contain about 50, 100, 110, 120, 130, 140, 150, 160, 170, 180, 190, or 200 mg of pharmaceutical composition. In certain aspects the amount of pharmaceutical composition is an amount set forth in Table 8.

In another aspect is an anhydrous pharmaceutical composition and dosage form. Such anhydrous forms can reduce or eliminate degradation of active ingredients in the composition resulting from heat or water exposure. For example, the addition of water (e.g., 5 percent) is widely accepted in the pharmaceutical arts as a means of simulating shelf-life, e.g., long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. The effect of water on a formulation can be of great significance since moisture or humidity are commonly encountered during manufacture, handling, packaging, storage, shipment, and use of formulations. Without being limited by a particular theory, it was found that Compound A or enantiomer or a mixture of enantiomers thereof, a pharmaceutically acceptable stereoisomer, a pharmaceutically acceptable salt, prodrug, solvate, hydrate, co-crystal, clathrate, or polymorph thereof can be easily degraded by hydrolysis, and thus, all ingredients in the dosage forms should be anhydrous or have a very low water content.

Anhydrous dosage forms described herein can be prepared and stored such that the anhydrous nature is maintained. Accordingly, in some embodiments, anhydrous dosage forms are packaged using materials known to prevent exposure to water such that they can be included in suitable formulary kits, including those described herein. Examples of suitable packaging include, but are not limited to, hermetically sealed foils, plastic or the like, unit dose containers, blister packs, and strip packs.

In this regard, also provided herein is a method of preparing a dosage form (e.g., a solid pharmaceutical formulation) that includes an active ingredient through admixing the active ingredient (e.g., Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof) and a pharmaceutically acceptable excipient described herein under anhydrous or low moisture/humidity conditions (e.g., less than about 5% water), wherein the ingredients are substantially free of water. The method can further include packaging the anhydrous or non-hygroscopic solid dosage form under low moisture conditions (e.g., less than about 5% water). By using such conditions, the risk of contact with water is reduced and the degradation of the active ingredient can be prevented or substantially reduced.

In some embodiments, because it is can be typical to obtain Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof at a purity of less than 100%, the formulations and dosage forms provided herein may be defined as compositions, formulations, or dosage forms that comprise Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides the potency of a specified amount of 100% pure Compound A.

In one aspect is an oral dosage form which weighs about 100 mg and includes Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 0.5 mg Compound A and a pharmaceutically acceptable carrier or excipient as described herein.

In another aspect is an oral dosage form which weighs about 100 mg and includes Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 1 mg Compound A and a pharmaceutically acceptable carrier or excipient as described herein.

In yet another aspect is an oral dosage form which weighs about 200 mg and includes Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 2 mg Compound A and a pharmaceutically acceptable carrier or excipient as described herein.

In still another aspect is an oral dosage form which weighs about 120 mg and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 3 mg Compound A and a pharmaceutically acceptable carrier or excipient as described herein.

In another aspect is an oral dosage form which weighs about 140 mg and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 3.5 mg Compound A and a pharmaceutically acceptable carrier or excipient as described herein.

In another aspect is an oral dosage form which weighs about 160 mg and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 4 mg Compound A and a pharmaceutically acceptable carrier or excipient as described herein.

In still another aspect is an oral dosage form which weighs about 200 mg and includes Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof at an amount that provides 5 mg Compound A and a pharmaceutically acceptable carrier or excipient as described herein.

In one embodiment, the pharmaceutically acceptable carrier or excipient further comprises starch, cellulose, mannitol, or a mixture thereof. In one embodiment cellulose in microcrystalline cellulose. In another embodiment microcrystalline cellulose is silicified microcrystalline cellulose. In a further embodiment mocrocrystalline cellulose is low moisture grade microcrystalline cellulose. In a further embodiment microcrystalline cellulose is a mixture of silicified microcrystalline cellulose and low moisture grade microcrystalline cellulose. In one embodiment, the mannitol is spray dried mannitol.

In one embodiment, the oral dosage form is an oral dosage form as set forth in Table 8.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.01 to about 10 weight percent or about 0.1 to about 10 weight percent of total weight of the dosage form. Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.01 to about 5 weight percent of total weight of the dosage form. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.01 to about 3 weight percent of total weight of the dosage form. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.05 to about 3 weight percent of total weight of the dosage form. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.01 to about 1 weight percent of total weight of the dosage form.

In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.1 to about 3 weight percent of total weight of the dosage form. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.5 to about 3 weight percent of total weight of the dosage form. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.1 to about 3 weight percent of total weight of the dosage form.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 0.01, 0.02, 0.03, 0.04, 0.05, 0.06, 0.07, 0.08, 0.09 or 0.1 weight percent of total weight of the dosage form.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be present in the dosage form at an amount of about 1, 2, 3, 4, or 5 weight percent of total weight of the dosage form.

In one embodiment, the active ingredient and binder or filler are directly blended as described herein elsewhere. The pharmaceutically acceptable carrier or excipient can include starch, cellulose, mannitol or a mixture thereof. In one embodiment cellulose in microcrystalline cellulose. In another embodiment microcrystalline cellulose is silicified microcrystalline cellulose. In a further embodiment mocrocrystalline cellulose is low moisture grade microcrystalline cellulose. In a further embodiment microcrystalline cellulose is a mixture of silicified microcrystalline cellulose and low moisture grade microcrystalline cellulose. In one embodiment, the mannitol is spray dried mannitol. Thus, in embodiments, the binder or filler is starch (e.g., pregelatinized starch), cellulose (e.g., microcrystalline cellulose), or mannitol (e.g., spray dried mannitol) and is not lactose. The binder or filler can be starch (e.g., pregelatinized starch). The binder or filler can be a combination of starch (e.g., pregelatinized starch) and mannitol. The binder or filler can be cellulose (e.g., microcrystalline cellulose). The binder or filler can be a combination of cellulose (e.g., microcrystalline cellulose) and mannitol (e.g., spray dried mannitol). The binder or filler is not lactose.

The binder or filler can be present in the dosage form at an amount of about 90 to about 99.9, 91 to about 99.9, 92 to about 99.9, 93 to about 99.9, 94 to about 99.9, 95 to about 99.9, 96 to about 99.9, 97 to about 99.9, or 98 to about 99.9 weight percent of total weight of the dosage form. The binder or filler can be present in the dosage form at an amount of about 90 to about 99 weight percent of total weight of the dosage form. The binder or filler can be present in the dosage form at an amount of about 92 to about 99.9 weight percent of total weight of the dosage form. The binder or filler can be present in the dosage form at an amount of about 93 to about 97 weight percent of total weight of the dosage form. The binder or filler can be present in the dosage form at an amount of about 90 to about 96 weight percent of total weight of the dosage form. The binder or filler can be present in the dosage form at an amount of about 90 to about 95 weight percent of total weight of the dosage form. The binder or filler can be present in the dosage form at an amount of about 91 to about 93 weight percent of total weight of the dosage form. The binder or filler can be present in the dosage form at an amount of about 90, 91, 92, 93, 94, 95, 96, 97, 98, 99, or 99.9 weight percent of total weight of the dosage form. In certain embodiments the binder or filler is present in the dosage form at an amount of about 90, 91, 92, or 93 weight percent of total weight in the dosage form.

In embodiments, the dosage forms provided herein include cellulose and mannitol as a binder or filler present in amounts as described herein. The cellulose can be microcrystalline cellulose (e.g., silicified microcrystalline cellulose or Type PH-102). In such embodiments, the cellulose can be present in the dosage form at an amount of about 45 to 75 weight percent of the total weight of the dosage form. The cellulose can be present in the dosage form at an amount of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 weight percent of the total weight of the dosage form. In certain embodiments, the cellulose is present at an amount of about 50-56 weight percent of the total weight of the dosage form. In certain embodiments, the cellulose is present at an amount of about 65-75 weight percent of the total weight of the dosage form. In such embodiments, mannitol can be present in the dosage form at an amount of about 20 to 45 weight percent of the total weight of the dosage form. In certain embodiments, the mannitol is present at an amount of about 25 weight percent of the total weight of the dosage form. In certain embodiments, the mannitol is present at an amount of about 41 weight percent of the total weight of the dosage form.

When the dosage form includes cellulose and mannitol, the cellulose and mannitol can be present in the dosage form at a total amount of about 90 to 99 weight percent of the total weight of the dosage form. In certain instances, when the dosage form includes cellulose and mannitol, the cellulose and mannitol can be present in the dosage form at a total amount of about 90 to 94 (e.g., 90, 91, 92, 93, 94) weight percent of the total weight of the dosage form. In such embodiments, the cellulose and mannitol can be present in the dosage form at a total amount of about 93 to 98 weight percent of the total weight of the dosage form and the dosage form weighs about 100 mg and provides about 1 mg of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. In some embodiments, the cellulose and mannitol can be present in the dosage form at a total amount of about 90 to 95 weight percent of the total weight of the dosage form and the dosage form weighs about 100 mg and provides about 1 mg of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. In certain embodiments, the cellulose and mannitol are present in amounts set forth in Table 2 or Table 8.

The amount of cellulose in the dosage form can be about 69 mg (e.g., 69.73 mg) and the amount of mannitol can be about 24 mg (e.g., 24.75 mg). The amount of cellulose in the dosage form can be about 73 mg (e.g., 73.37 mg) and the amount of mannitol can be about 24 mg (e.g., 24.75 mg). The amount of cellulose in the dosage form can be about 55 mg (e.g., 55.7 mg) and the amount of mannitol can be about 41 mg (e.g., 41.42 mg). The amount of cellulose in the dosage form can be about 51 mg (e.g., 51.7 mg) and the amount of mannitol can be about 41 mg (e.g., 41.42 mg).

The amount of cellulose in the dosage form can be about 52 mg (e.g., 52.267 mg) and the amount of mannitol can be about 41 mg (e.g., 41.42 mg). The amount of cellulose in the dosage form can be about 103 mg (e.g., 103.406 mg) and the amount of mannitol can be about 82 mg (e.g., 82.84 mg). The amount of cellulose in the dosage form can be about 60 mg (e.g., 60.019 mg) and the amount of mannitol can be about 49 mg (e.g., 49.70 mg). The amount of cellulose in the dosage form can be about 70 mg (e.g., 70.022 mg) and the amount of mannitol can be about 57 mg (e.g., 57.983 mg).

The amount of cellulose in the dosage form can be about 80 mg (e.g., 80.025 mg) and the amount of mannitol can be about 66 mg (e.g., 66.267 mg). The amount of cellulose in the dosage form can be about 100 mg (e.g., 100.031 mg) and the amount of mannitol can be about 82 mg (e.g., 82.834 mg).

When the dosage form includes cellulose and mannitol, the cellulose and mannitol can be present in the dosage form at a total amount of about 91 to 97 weight percent of the total weight of the dosage form. In such embodiments, the cellulose and mannitol can be present in the dosage form at a total amount of about 91 to 97 weight percent of the total weight of the dosage form and the dosage form weighs about 120 mg and provides about 3 mg of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. The cellulose and mannitol can be present in a total amount of about 92, 93, 94, 95, 96, 97, or 98 weight percent of the total weight of the dosage form. In certain embodiments, the cellulose and mannitol are present in amounts set forth in Table 2.

The amount of cellulose in the dosage form can be about 81 mg (e.g., 81.22 mg) and the amount of mannitol can be about 29 mg (e.g., 29.7 mg). The amount of cellulose in the dosage form can be about 86 mg (e.g., 86.02 mg) and the amount of mannitol can be about 29 mg (e.g., 29.7 mg). The amount of cellulose in the dosage form can be about 64 mg (e.g., 64.82 mg) and the amount of mannitol can be about 49 mg (e.g., 49.7 mg). The amount of cellulose in the dosage form can be about 60 mg (e.g., 60.02 mg) and the amount of mannitol can be about 49 mg (e.g., 49.7 mg).

In embodiments, the dosage forms provided herein include starch (e.g., pregelatinized starch) and mannitol as a binder or filler present in amounts as described herein. In such embodiments, the starch can be present in the dosage form at an amount of about 45 to 70 weight percent of the total weight of the dosage form. The starch can be present in the dosage form at an amount of about 50 to 52 weight percent of the total weight of the dosage form. The starch can be present in the dosage form at an amount of about 66 to 69 weight percent of the total weight of the dosage form. In such embodiments, the mannitol can be present in the dosage form at an amount of about 20 to 45 weight percent of the total weight of the dosage form. In certain embodiments, the mannitol is present at an amount of about 25 weight percent of the total weight of the dosage form. In certain embodiments, the mannitol is present at an amount of about 41 weight percent of the total weight of the dosage form.

When the dosage form includes starch and mannitol, the starch and mannitol can be present in the dosage form at a total amount of about 90 to 94 weight percent of the total weight of the dosage form. The starch and mannitol can be present in a total amount of about 90, 91, 92, or 93 weight percent of the total weight of the dosage form. In embodiments, the dosage form includes starch and mannitol present at a total amount of about 93 weight percent of the total weight of the dosage form and the dosage form weighs about 100 mg and provides about 1 mg of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. In certain embodiments, the starch and mannitol are present in amounts set forth in Table 2.

The amount of starch in the dosage form can be about 68 mg (e.g., 68.37 mg) and the amount of mannitol can be about 24 mg (e.g., 24.75 mg). The amount of starch in the dosage form can be about 51 mg (e.g., 51.7 mg) and the amount of mannitol can be about 41 mg (e.g., 41.42 mg).

When the dosage form described herein includes starch and mannitol, the starch and mannitol can be present in the dosage form at a total amount of about 91 weight percent of the total weight of the dosage form. In embodiments, the dosage form described herein includes starch and mannitol present at a total amount of about 91 weight percent of the total weight of the dosage form and the dosage form weighs about 120 mg and provides about 3 mg of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof. In certain embodiments, the starch and mannitol are present in a dosage form as described herein in amounts set forth in Table 2.

The amount of starch in the dosage form described herein can be about 80 mg (e.g., 80.02 mg) and the amount of mannitol can be about 29 mg (e.g., 29.7 mg). The amount of starch in the dosage form can be about 60 mg (e.g., 60.02 mg) and the amount of mannitol can be about 49 mg (e.g., 49.7 mg). In certain embodiments, the starch and mannitol are present in amounts set forth in Table 2.

The lubricant of the dosage forms described herein can be present in an amount of about 0 (e.g., absent) to 2 weight percent of the total weight of the dosage form described herein. The lubricant of the dosage forms described herein can be present in an amount of about 0 to 1 weight percent of the total weight of the dosage form described herein. The lubricant of the dosage forms described herein can be present in an amount of about 0.5 to 2 weight percent of the total weight of the dosage form described herein. The lubricant of the dosage forms described herein can be present in an amount of about 0.5 to 1 weight percent of the total weight of the dosage form described herein. The lubricant can be present in an amount of about 0.75 weight percent of the total weight of the dosage form described herein. In embodiments, the lubricant can be present in an amount of about 0.75 weight percent of the total weight of the dosage form described herein and the dosage form weighs about 100 or 120 mg. In embodiments, when dosage form described herein weighs about 100 mg the lubricant is present in an amount of about 0.75 mg. In embodiments, when dosage form described herein weighs about 120 mg the lubricant is present in an amount of about 0.9 mg. In embodiments, when dosage form described herein weighs about 140 mg the lubricant is present in an amount of about 1.05 mg. In embodiments, when dosage form described herein weighs about 160 mg the lubricant is present in an amount of about 1.6 mg. In embodiments, when dosage form described herein weighs about 200 mg the lubricant is present in an amount of about 1.5 mg.

The lubricant can be a lubricant known by those in art. Useful lubricants for the dosage forms described herein include those described in *Handbook of Pharmaceutical Excipients*, Rowe R. C., Shesky P. J., and Quinn M. E., 6$^{th}$ Ed., The Pharmaceutical Press, RPS Publishing (2009), which is incorporated herein in its entirely and for all purposes. The lubricant can be glyceryl behenate, sodium stearyl fumarate, glyceryl monostearate, glyceryl palmitostearate, myristic acid, palmitic acid, poloxamer, PEG, PEG-stearate, benzoate (e.g., sodium or potassium benzoate), talc, or stearic acid. In certain embodiments, the dosage forms described herein do not include metal stearates. Thus, in certain embodiments, the dosages forms described herein do not include magnesium stearate. In certain embodiments, the dosage forms described herein do not include talc. Without being bound by any particular theory, certain lubricants react with the HCl salt of Compound A, thereby destabilizing the compound. In preferred embodiments, stearic acid is the lubricant of the dosage forms described herein.

The dosage forms described herein can further include a disintegrant. Useful disintegrants herein include those described in *Handbook of Pharmaceutical Excipients*, Rowe R. C., Shesky P. J., and Quinn M. E., 6$^{th}$ Ed., The Pharmaceutical Press, RPS Publishing (2009), which is incorporated herein in its entirely and for all purposes. The disintegrant can be a disintegrant known by those in the art including for example, crospovidone Type A or colloidal silicon dioxide, or a combination thereof. In certain embodiments, the dosage forms described herein do not include croscarmellose sodium. Without being bound by any particular theory, some disintegrants react with the HCl salt of Compound A, thereby destabilizing the compound. In embodiments, the dosage forms described herein do not include magnesium stearate and sodium croscarmellose because, without being bound by any particular theory, these agents react with and destabilize Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in the dosage form.

When the dosage forms described herein include a disintegrant, the disintegrant can be present at an amount of about 1 to 5 weight percent of the total weight of the dosage form. The disintegrant can be present at an amount of about 1 to 4 weight percent of the total weight of the dosage form described herein. In embodiments, the disintegrant is present at an amount of about 1 weight percent of the total weight of the dosage form described herein. In embodiments, the disintegrant is present at an amount of about 4 weight percent of the total weight of the dosage form described herein. When the dosage form described herein weighs about 100 mg as described herein, the disintegrant can be present at an amount of about 1 mg or about 4 mg. When the dosage form weighs described herein about 120 mg as described herein, the disintegrant can be present at an amount of about 1.2 mg or about 4.8 mg. When the dosage form weighs described herein about 140 mg as described herein, the disintegrant can be present at an amount of about 1.2 mg or about 5.6 mg. When the dosage form weighs described herein about 160 mg as described herein, the disintegrant can be present at an amount of about 1.2 mg or about 6.4 mg. When the dosage form weighs described herein about 200 mg as described herein, the disintegrant can be present at an amount of about 1.2 mg or about 8.0 mg.

When the dosage forms described herein include two or more disintegrants as described herein in combination, the total weight percent of the combination can be about 5% of the total weight of the dosage form.

The dosage forms described herein can include one or more pharmaceutically acceptable excipients selected from the group consisting of: colloidal silicon dioxide, microcrystalline cellulose, crospovidone, mannitol, pregelatinized starch, stearic acid, gelatin, acacia, alginic acid, castor oil, hydrogenated, cellulose acetate, cellulose powder, chitosan, citric acid, copovidone, corn starch, cyclodextrins, dextrates, dextrin, dextrose, erythritol, ethylcellulose, fructose, glyceryl behenate, glyceryl monooleate, glyceryl monostearate, glyceryl palmitostearate, guar gum, hydrophobic colloidal silica, hydroxyethyl cellulose, hydroxyethylmethyl cellulose, hydroxypropyl cellulose (e.g., low substituted), hydroxypropyl starch, hypromellose, hypromellose acetate succinate, isomalt, lactitol, lauric acid, leucine, maltodextrin, maltose, methylcellulose, myristic acid, octyldodecanol, palmitic acid, poloxamer, polydextrose, polyethylene oxide, polyvinyl alcohol, povidone, sorbitol, silicified microcrystalline cellulose, starch, sucrose, sugar, trehalose, vegetable oil, hydrogenated, and xylitol. In certain embodiments, the dosage forms described herein include one or more one or more pharmaceutically acceptable excipients selected from the group consisting of: colloidal silicon dioxide, microcrystalline cellulose, crospovidone, mannitol, pregelatinized starch, stearic acid, and gelatin.

The dosage form can be a dosage form as set forth in Table 2. Thus, in embodiments, the dosage form is a form represented by the designations in Table 2 (e.g., F1, F2, F3, F4, F5, F6, or F7). The dosage form can be F1. The dosage form can be F2. The dosage form can be F3. In certain embodiments, the dosage form is F4. In certain embodiments, the dosage form is F5. The dosage form can be F6. The dosage form can be F7. The dosage form can be a dosage form as set forth in Table 8.

In one aspect is an oral dosage form that includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 0.5, 1, 2, 3, 3.5, 4, or 5 mg Compound A and a pharmaceutically acceptable carrier or excipient that includes a lubricant as described herein. The lubricant and pharmaceutically acceptable excipient can be present at an amount as described herein (e.g., cellulose, mannitol, colloidal silicone).

In one aspect is an oral dosage form that weighs about 100 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 0.5 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In another aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 0.5 mg Compound A, about 52.26 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In another aspect, the dosage form does not include sodium croscarmellose as described herein. In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 0.5 mg Compound A, about 52.26 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In yet another aspect, the dosage form does not include magnesium stearate as described herein. In yet another aspect, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 0.5 mg Compound A, about 52.26 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In yet another aspect, the dosage form does not include magnesium stearate and croscarmellose as described herein. In yet another aspect, the dosage form does not include magnesium stearate and croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 0.5 mg Compound A, about 52.26 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In one aspect is an oral dosage form that weighs about 100 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 1 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In another aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 55.7 mg microcrystalline cellulose (Type PH-102), about 41.42 mg mannitol, about 1 mg colloidal silicon dioxide, and about 750 µg stearic acid in a 100 mg total weight dosage form (e.g., a capsule).

In another aspect, the dosage form does not include sodium croscarmellose as described herein. In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 55.7 mg microcrystalline cellulose (Type PH-102), about 41.42 mg mannitol, about 1 mg colloidal silicon dioxide, and about 750 µg magnesium stearate in a 100 mg total weight dosage form (e.g., a capsule).

In another aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 51.7 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In another embodiment, the dosage form does not include sodium croscarmellose as described herein. In another embodiment, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 51.7 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In another embodiment, the dosage form does not include magnesium stearate as described herein. In another embodiment, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 51.7 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In another embodiment, the dosage form does not include sodium croscarmellose and magnesium stearate as described herein. In another embodiment, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 1 mg Compound A, about 51.7 mg microcrystalline cellulose (Type PH-102), about 41.42 mg mannitol, about 4 mg crospovidone, about 1 mg colloidal silicon dioxide, and about 750 µg stearic acid in a 100 mg total weight dosage form (e.g., a capsule).

In one aspect is an oral dosage form that weighs about 200 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 2 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In one aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 2 mg Compound A, about 103.4 mg microcrystalline cellulose (Type PH-102), about 82.84 mg mannitol, about 8 mg crospovidone, about 2 mg colloidal silicon dioxide, and about 1.5 mg stearic acid in a 200 mg total weight dosage form (e.g., a capsule).

In another aspect, the dosage form does not include sodium croscarmellose as described herein. In another aspect the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 2 mg Compound A, about 103.4 mg microcrystalline cellulose (Type PH-102), about 82.84 mg mannitol, about 8 mg crospovidone, about 2 mg colloidal silicon dioxide, and about 1.5 mg stearic acid in a 200 mg total weight dosage form (e.g., a capsule).

In yet another embodiment, the dosage form does not include magnesium stearate as described herein. In yet another embodiment, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 2 mg Compound A, about 103.4 mg microcrystalline cellulose (Type PH-102), about 82.84 mg mannitol, about 8 mg crospovidone, about 2 mg colloidal silicon dioxide, and about 1.5 mg stearic acid in a 200 mg total weight dosage form (e.g., a capsule).

In yet another embodiment, the dosage form does not include sodium croscarmellose and magnesium stearate as described herein. In yet another embodiment, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 2 mg Compound A, about 103.4 mg microcrystalline cellulose (Type PH-102), about 82.84 mg mannitol, about 8 mg crospovidone, about 2 mg colloidal silicon dioxide, and about 1.5 mg stearic acid in a 200 mg total weight dosage form (e.g., a capsule).

In one aspect is an oral dosage form that weighs about 120 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 3 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In one aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3 mg Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, about 60.01 mg microcrystalline cellulose (Type PH-102), about 49.7 mg mannitol, about 4.8 mg crospovidone, about 1.2 mg colloidal silicon dioxide, and about 900 μg stearic acid in a 120 mg total weight dosage form (e.g., a capsule).

In another aspect, the dosage form does not include sodium croscarmellose as described herein. In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3 mg Compound A, about 60.01 mg microcrystalline cellulose (Type PH-102), about 49.7 mg mannitol, about 4.8 mg crospovidone, about 1.2 mg colloidal silicon dioxide, and about 900 μg stearic acid in a 120 mg total weight dosage form (e.g., a capsule).

In yet another aspect, the dosage form does not include magnesium stearate as described herein. In yet another aspect, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3 mg Compound A, about 60.01 mg microcrystalline cellulose (Type PH-102), about 49.7 mg mannitol, about 4.8 mg crospovidone, about 1.2 mg colloidal silicon dioxide, and about 900 μg stearic acid in a 120 mg total weight dosage form (e.g., a capsule).

In yet another aspect, the dosage form does not include sodium croscarmellose and magnesium stearate as described herein. In yet another aspect, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3 mg Compound A, about 60.01 mg microcrystalline cellulose (Type PH-102), about 49.7 mg mannitol, about 4.8 mg crospovidone, about 1.2 mg colloidal silicon dioxide, and about 900 μg stearic acid in a 120 mg total weight dosage form (e.g., a capsule).

In one aspect is an oral dosage form that weighs about 140 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 3.5 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In one aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3.5 mg Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, about 70.02 mg microcrystalline cellulose (Type PH-102), about 57.98 mg mannitol, about 5.6 mg crospovidone, about 1.4 mg colloidal silicon dioxide, and about 1.05 mg stearic acid in a 140 mg total weight dosage form (e.g., a capsule).

In another aspect, the dosage form does not include sodium croscarmellose as described herein. In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3.5 mg Compound A, about 70.02 mg microcrystalline cellulose (Type PH-102), about 57.98 mg mannitol, about 5.6 mg crospovidone, about 1.4 mg colloidal silicon dioxide, and about 1.05 mg stearic acid in a 140 mg total weight dosage form (e.g., a capsule).

In yet another aspect, the dosage form does not include magnesium stearate as described herein. In yet another aspect, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3.5 mg Compound A, about 70.02 mg microcrystalline cellulose (Type PH-102), about 57.98 mg mannitol, about 5.6 mg crospovidone, about 1.4 mg colloidal silicon dioxide, and about 1.05 mg stearic acid in a 140 mg total weight dosage form (e.g., a capsule).

In yet another aspect, the dosage form does not include sodium croscarmellose and magnesium stearate as described herein. In yet another aspect, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 3.5 mg Compound A, about 70.02 mg microcrystalline cellulose (Type PH-102), about 57.98 mg mannitol, about 5.6 mg crospovidone, about 1.4 mg colloidal silicon dioxide, and about 1.05 mg stearic acid in a 140 mg total weight dosage form (e.g., a capsule).

In one aspect is an oral dosage form that weighs about 160 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 4 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In one aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 4 mg Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, about 80.02 mg microcrystalline cellulose (Type PH-102), about 66.26 mg mannitol, about 6.4 mg crospovidone, about 1.6 mg colloidal silicon dioxide, and about 1.2 mg stearic acid in a 160 mg total weight dosage form (e.g., a capsule).

In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 4 mg Compound A, about 80.02 mg microcrystalline cellulose (Type PH-102), about 66.26 mg mannitol, about 6.4 mg crospovidone, about 1.6 mg colloidal silicon dioxide, and about 1.2 mg stearic acid in a 160 mg total weight dosage form (e.g., a capsule).

In yet another aspect, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 4 mg Compound A, about 80.02 mg microcrystalline cellulose (Type PH-102), about 66.26 mg mannitol, about 6.4 mg crospovidone, about 1.6 mg colloidal silicon dioxide, and about 1.2 mg stearic acid in a 160 mg total weight dosage form (e.g., a capsule).

In yet another aspect, the dosage form does not include sodium croscarmellose and magnesium stearate as described herein. In yet another aspect, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 4 mg Compound A, about 80.02 mg microcrystalline cellulose (Type PH-102), about 66.26 mg mannitol, about 6.4 mg crospovidone, about 1.6 mg colloidal silicon dioxide, and about 1.2 mg stearic acid in a 160 mg total weight dosage form (e.g., a capsule).

In one aspect is an oral dosage form that weighs about 100 mg and includes: Compound A (3-(5-amino-2-methyl-4-oxo-4H-quinazolin-3-yl)-piperidine-2,6-dione), or enantiomer or a mixture of enantiomers thereof, a pharmaceutically acceptable stereoisomer, a pharmaceutically acceptable salt, prodrug, solvate, hydrate, co-crystal, clathrate, or polymorph thereof, at an amount that provides 5 mg Compound A and a pharmaceutically acceptable carrier or excipient that includes a lubricant as described herein. In one embodiment, the carrier or excipient further comprises starch, cellulose, mannitol, or a mixture thereof. In one embodiment, the cellulose is microcrystalline cellulose. In one embodiment, the microcrystalline cellulose is low moisture grade microcrystalline cellulose. In one embodiment, the mannitol is spray dried mannitol. In one embodiment, the dosage form comprises HCl salt of Compound A.

In one aspect, the dosage form includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 5 mg Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, about 100.03 mg microcrystalline cellulose (Type PH-102), about 82.83 mg mannitol, about 8 mg crospovidone, about 2 mg colloidal silicon dioxide, and about 1.5 mg stearic acid in a 160 mg total weight dosage form (e.g., a capsule).

In another aspect, the dosage form does not include sodium croscarmellose as described herein. In another aspect, the dosage form does not include sodium croscarmellose as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 5 mg Compound A, about 100.03 mg microcrystalline cellulose (Type PH-102), about 82.83 mg mannitol, about 8 mg crospovidone, about 2 mg colloidal silicon dioxide, and about 1.5 mg stearic acid in a 160 mg total weight dosage form (e.g., a capsule).

In yet another aspect, the dosage form does not include magnesium stearate as described herein. In yet another aspect, the dosage form does not include magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 5 mg Compound A, about 100.03 mg microcrystalline cellulose (Type PH-102), about 82.83 mg mannitol, about 8 mg crospovidone, about 2 mg colloidal silicon dioxide, and about 1.5 mg stearic acid in a 160 mg total weight dosage form (e.g., a capsule).

In yet another aspect, the dosage form does not include sodium croscarmellose and magnesium stearate as described herein. In yet another aspect, the dosage form does not include sodium croscarmellose and magnesium stearate as described herein and includes Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, present at an amount that provides about 5 mg Compound A, about 100.03 mg microcrystalline cellulose (Type PH-102), about 82.83 mg mannitol, about 8 mg crospovidone, about 2 mg colloidal silicon dioxide, and about 1.5 mg stearic acid in a 160 mg total weight dosage form (e.g., a capsule).

Dosage forms described herein can be stable from about 1 day to about 2 years. Dosage forms described herein can be stable from about 1 day to about 1 year. Dosage forms described herein can be stable from about 30 days to about 2 years. Dosage forms described herein can be stable from about 30 days to about 1 year. Dosage forms described herein can be stable for greater than 1 day to greater than about 2 years. Dosage forms described herein can be stable for greater than 1 day to greater than 1 year. Dosage forms described herein can be stable for greater than 10, 15, 20, 30, 45, 50, 60, 70, 80, 90, 100, 120, 150, 180, 210, 240, 270, 300, 330, or 360 days. In one embodiment, the dosage form is stable for at least 90 days.

Also provided herein are dosage forms described herein that are co-administered with one or more second active ingredients. In one embodiment, the dosage form described herein further includes the second active agent (e.g., a single unit dosage formulated to contain both Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof and a second active agent described herein). In another embodiment, the dosage forms described herein are co-administered simultaneously (as described herein) or sequentially (as described herein) with a separately formulated dosage of a second active agent described herein (e.g., a single unit dosage described herein and a second separate dosage of a second active agent described herein). The co-administered one or more second active ingredients can work synergistically with Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in the treatment of particular types diseases or disorders, and conditions and symptoms associated with such diseases or disorders.

Exemplary second active agents useful in treating cancer in combination with the dosage form described herein vary depending on the specific indication to be treated, prevented or managed. A second active agent can be an anti-cancer agent. "Anti-cancer agent" refers to a composition (e.g. compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer.

5.3 Process for Making Dosage Forms

Dosage forms provided herein can be prepared by any of the methods of pharmacy, but all methods include the step of bringing the active ingredient into association with the pharmaceutically acceptable excipient, which constitutes one or more necessary ingredients (such as binder or filler, disintegrants, or lubricants). In general, the compositions are prepared by uniformly admixing (e.g., direct blend) the active ingredient with liquid excipients or finely divided solid excipients or both, and then, if necessary, shaping the product into the desired presentation (e.g., compaction such as roller-compaction). If desired, tablets can be coated by standard aqueous or non-aqueous techniques.

A dosage form provided herein can be prepared by compression or molding, optionally with one or more accessory ingredients. Compressed tablets can be prepared by compressing in a suitable machine the active ingredient in a free-flowing form such as powder or granules, optionally mixed with an excipient as above or a surface active or dispersing agent. Molded tablets can be made by molding in a suitable machine a mixture of the powdered compound moistened with an inert liquid diluent. Encapsulation of the dosage forms provided herein can be done using capsules of methylcellulose, calcium alginate, or gelatin.

In some embodiments, the active ingredients and excipients are directly blended and loaded into, for example, a capsule, or compressed directly into tablets. A direct-blended dosage form may be more advantageous than a compacted (e.g., roller-compacted) dosage form in certain instances, since direct-blending can reduce or eliminate the harmful health effects that may be caused by airborne particles of ingredients during the manufacture using compaction process.

Direct blend formulations may be advantageous in certain instances because they require only one blending step, that of the active and excipients, before being processed into the final dosage form, e.g., tablet or capsule. This can reduce the production of airborne particle or dust to a minimum, while roller-compaction processes may be prone to produce dust. In roller-compaction process, the compacted material is often milled into smaller particles for further processing. The milling operation can produce significant amounts of airborne particles, since the purpose for this step in manufacturing is to reduce the materials particle size. The milled material is then blended with other ingredients prior to manufacturing the final dosage form.

For certain active ingredients, in particular for a compound with a low solubility, the active ingredient's particle size is reduced to a fine powder in order to help increase the active ingredient's rate of solubilization. The increase in the rate of solubilization is often necessary for the active ingredient to be effectively absorbed in the gastrointestinal tract. However for fine powders to be directly-blended and loaded onto capsules, the excipients should preferably provide certain characteristics which render the ingredients suitable for the direct-blend process. Examples of such characteristics include, but are not limited to, acceptable flow characteristics. In one embodiment, therefore, provided herein is the use of, and compositions comprising, excipients which may provide characteristics, which render the resulting mixture suitable for direct-blend process, e.g., good flow characteristics.

Screening. The process for making the pharmaceutical compositions of the invention preferably includes the screening of the active ingredient and the excipient(s). In one embodiment, the active ingredient is passed through a screen having openings of about 200 microns to about 750 microns. In another embodiment, the active ingredient is passed through a screen with openings of about 200 microns to about 400 microns. In one embodiment, the active ingredient is passed through a screen having openings of about 300 to about 400 microns. Depending on the excipient(s) used, the screen openings vary. For example, disintegrants and binders are passed through openings of about 430 microns to about 750 microns, from about 600 microns to about 720 microns, or about 710 microns. Lubricants are typically passed through smaller openings, e.g., about 150 microns to about 250 microns screen. In one embodiment, the lubricant is passed through a screen opening of about 210 microns.

Pre-blending. After the ingredients are screened, the excipient and active ingredient are mixed in a diffusion mixer. In one embodiment, the mixing time is from about 1 minute to about 50 minutes, from about 5 minutes to about 45 minutes, from about 10 minutes to about 40 minutes, or from about 10 minutes to about 25 minutes. In another embodiment, the mixing time is about 15 minutes.

When more than one excipient is used, the excipients may be admixed in a tumble blender for about 1 minute to about 20 minutes, or for about 5 minutes to about 10 minutes, prior to mixing with the active ingredient.

Roller Compaction. In one embodiment, the pre-blend may optionally be passed through a roller compactor with a hammer mill attached at the discharge of the compactor.

Final Blend. When a lubricant, e.g., stearic acid, is used, the lubricant is mixed with the pre-blend at the end of the process to complete the pharmaceutical composition. This additional mixing is from about 1 minute to about 10 minutes, or from about 3 minutes to about 5 minutes.

Encapsulation. The formulation mixture is then encapsulated into the desired size capsule shell using, for example, a capsule filling machine or a rotary tablet press.

5.4 Kits

Pharmaceutical packs or kits which comprise pharmaceutical compositions or dosage forms provided herein are also provided. Exemplary kits include notice in the form prescribed by a governmental agency regulating the manufacture, use or sale of pharmaceuticals or biological products, which notice reflects approval by the agency of manufacture, use or sale for human administration. Kits herein can be useful for retaining the anhydrous nature of dosage forms described herein.

5.5 Methods of Treating

Further provided herein are methods of treating, preventing, or managing cancer by administering to a subject a dosage form described herein. In one aspect is a method of treating cancer by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof thereby treating or preventing cancer in a patient.

Further provided herein are oral dosage forms for use in methods of treating, preventing, or managing cancer by administering to a subject a dosage form described herein. In one aspect is a method of treating cancer by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof thereby treating or preventing cancer in a patient.

Further provided herein is a method of managing cancer by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof, thereby managing the cancer.

Further provided herein is an oral dosage form for use in a method of managing cancer by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof, thereby managing the cancer.

Provided herein are methods of treating or managing lymphoma. In one aspect is a method of treating or managing lymphoma (e.g., non-Hodgkin's lymphoma) by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof. Thus, also provided herein is a method of treating or managing non-Hodgkin's lymphoma by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof. In some embodiments, provided herein are methods for treating or managing non-Hodgkin's lymphoma (NHL), including but not limited to, diffuse large B-cell lymphoma (DLBCL), using prognostic factors and by administering an effective amount of Compound A, or an enantiomer or a mixture of enantiomers thereof, in a dosage form described herein to a patient in need thereof thereby treating or managing non-Hodgkin's lymphoma.

Also provided herein are methods of treating patients who have been previously treated for cancer but are non-responsive to standard therapies. In one aspect is a method of treating a non-responsive patient previously treated for cancer by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof. The methods described herein also include methods of treating patients regardless of patient's age, although some diseases or disorders are more common in certain age groups. The methods described herein further include methods of treating patients who have undergone surgery in an attempt to treat the disease or condition at issue. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma. The cancer can be non-Hodgkin's lymphoma or multiple myeloma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma. The solid tumor can be hepatocellular carcinoma. The solid tumor can be prostate cancer. The solid tumor can be ovarian cancer. The solid tumor can be glioblastoma. Thus, as described herein, methods directed to treating the above-referenced cancers independently in or combination are also included.

Provided herein are methods of treating, preventing, or managing cancer in patients with impaired renal function by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof, thereby treating, preventing, or managing cancer in the patient.

Provided herein are methods of treating, preventing, or managing relapsed/refractory multiple myeloma in patients with impaired renal function or a symptom thereof by administering a therapeutically effective amount of Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof, thereby treating, preventing, or managing relapsed/refractory multiple myeloma in the patient.

Thus provided herein are methods of preventing relapsed/refractory multiple myeloma in patients with impaired renal function or a symptom thereof by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof. Also provided herein are methods for treating relapsed/refractory multiple myeloma in patients with impaired renal function by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof. Provided herein are methods of managing relapsed/refractory multiple myeloma in patients with impaired renal function or a symptom thereof by administering an effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein to a patient in need thereof.

Therapeutic or prophylactic effective amounts of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, for use in the methods described herein include from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day. In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered in a dosage form described herein from about 0.5 to about 5 mg per day. In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered in a dosage form described herein from about 1 mg to about 5 mg per day.

Therapeutic or prophylactic effective amounts of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, for use in the methods described herein include about 0.1, about 0.2, about 0.3. about 0.5, about 1, about 2, about 3, about 4, about 5, about 10, about 15, about 20, about 25, about 30, about 40, about 45, about 50, about 60, about 70, about 80, about 90, about 100, or about 150 mg per day. In one embodiment, the therapeutic or prophylactic effective amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, for use in the methods described herein includes about 1, about 2, about 3, or about 5 mg per day.

Therapeutic or prophylactic effective amounts of Compound A or a pharmaceutically acceptable salt thereof, in a dosage form described herein for use in the methods described herein include from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day. In one embodiment, Compound A or a pharmaceutically acceptable salt thereof, is administered in a dosage form described herein from about 0.5 to about 5 mg every other day. In one embodiment, Compound A or a pharmaceutically acceptable salt thereof, is administered in a dosage form described herein from about 1 mg to about 5 mg per day.

Therapeutic or prophylactic effective amounts of Compound A or a pharmaceutically acceptable salt thereof, for use in the methods described herein include about 0.1, about 0.2, about 0.3. about 0.5, about 1, about 2, about 3, about 4, about 5, about 10, about 15, about 20, about 25, about 30, about 40, about 45, about 50, about 60, about 70, about 80, about 90, about 100, or about 150 mg per day. In one embodiment, the therapeutic or prophylactic effective amount of Compound A or a pharmaceutically acceptable salt thereof, for use in the methods described herein includes about 1, about 2, about 3, or about 5 mg per day.

A recommended daily dose range (e.g., therapeutic or prophylactic effective amount) of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein, for the conditions described herein can lie within the range of from about 0.5 mg to about 50 mg per day. Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein, can preferably be given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.01, 0.05, 0.1, 0.2, 0.3, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day. Specific doses per day can include 1 mg, 2 mg, 3 mg, or 5 mg per day. Specific doses per every other day include 0.01, 0.05, 0.1, 0.2, 0.3, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg. Specific doses per every other day can include 1 mg, 2 mg, 3 mg, or 5 mg per day.

A recommended starting dosage form compounds described herein in a dosage form described herein can be 0.01, 0.05, 0.1, 0.2, 0.3, 0.4, 0.5, 1, 2, 3, 4, 5, 10, 15, 20, 25 or 50 mg per day. In another embodiment, the recommended starting dosage form compounds described herein in a dosage form described herein may be 0.5, 1, 2, 3, 4, or 5 mg per day. In some patients, the dose may be escalated to 15, 20, 25, 30, 35, 40, 45 and 50 mg/day. Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 25 mg/day to patients with NHL (e.g., DLBCL). In a particular embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 10 mg/day to patients with NHL (e.g., DLBCL). Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 1 mg/day to patients with NHL (e.g., DLBCL). Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 3 mg/day to patients with NHL (e.g., DLBCL). Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 2 mg/day to patients with NHL (e.g., DLBCL). Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be administered in a dosage form described herein in an amount of about 5 mg/day to patients with NHL (e.g., DLBCL).

Therapeutic or prophylactic effective amount of compounds described herein in a dosage form described herein can be from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

The amount of an administered compound described herein can be described in terms of its sufficiency to provide a plasma concentration of the compound at steady state. In such embodiments, the plasma concentration of a compound described herein at steady state ranges from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of an administered compound described herein in a dosage form described herein is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

In certain embodiments, the amount of an administered compound described herein in a dosage form described herein is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of an administered compound described herein in a dosage form described herein is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of an administered compound described herein in a dosage form described herein is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein. In certain embodiments, the patient to be treated with one of the methods provided herein has been treated with anticancer therapy prior to the administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein. In certain embodiments, the patient to be treated with one of the methods provided herein has developed drug resistance to a previously used anticancer therapy.

Depending on the disease to be treated and the subject's condition, Compound A, an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered orally in a dosage form described herein to a patient in need thereof. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered parenterally in a dosage form described herein to a patient in need thereof. In yet another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered intravenously to a patient in need thereof.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, can be delivered as a single dose such as, e.g., a single bolus injection such as for example by oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein, can be administered once daily (QD), or divided into multiple daily doses such as twice daily (BID), three times daily (TID), and four times daily (QID). In addition, the administration can be continuous (e.g., daily for consecutive days or every day), intermittent, e.g., in cycles (e.g., including days, weeks, or months of rest without drug).

In some embodiments, the frequency of administration is in the range of about a daily dose to about a monthly dose. Frequency of administration as used herein refers to administration of compounds described herein, in a dosage form described herein, to a patient in need thereof. In certain embodiments, administration is once a day, twice a day, three times a day, four times a day, once every other day, twice a week, once every week, once every two weeks, once every three weeks, or once every four weeks. In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once a day. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered twice a day. In yet another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered three times a day. In still another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered four times a day.

In certain embodiments, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once per day from one day to six months, from one week to three months, from one week to four weeks, from one week to three weeks, or from one week to two weeks. In certain embodiments, Compound A, or a pharmaceutically acceptable salt or solvate thereof, in a dosage form described herein is administered once per day for one week, two weeks, three weeks, or four weeks. In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once per day for one week. In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once per day for two weeks. In yet another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once per day for three weeks. In still another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered once per day for four weeks.

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid, or reduce the side effects of one of the therapies, and/or improves the efficacy of the treatment.

Consequently, in certain embodiments, a compound provided herein (e.g., Compound A) is administered daily in a single or divided doses in a four to six week cycle with a rest period of about a week or two weeks. The cycling method further allows the frequency, number, and length of dosing cycles to be increased. Thus, encompassed herein in certain embodiments is the administration of a compound provided herein for more cycles than are typical when it is administered alone. In certain embodiments, a compound provided herein is administered for a greater number of cycles that would typically cause dose-limiting toxicity in a patient to whom a second active ingredient is not also being administered.

In other embodiments, the compound of Formula I, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered once a day for five days, followed by two off days in a seven days cycle. In one embodiment, the seven days cycle is repeated four times in a 28 days cycle. The 28 days cycle can be repeated one, two, three, four, five, six, seven, eight, nine, ten, or more times.

In another embodiment, the compound of Formula I, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, is administered once a day for 21 days, followed by 7 off days in a 28 days cycle. The cycle can be repeated one, two, three, four, five, six, seven, eight, nine, ten, or more times.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein can also be combined or used in combination (e.g., co-administered) with other therapeutic agents useful in the treatment or prevention of cancer described herein.

As used herein, the terms "in combination" and co-administration are used interchangeably and include the use of more than one therapy (e.g., one or more prophylactic or therapeutic agents). However, the use of the terms does not restrict the order in which therapies (e.g., prophylactic or therapeutic agents) are administered to a patient with a disease or disorder as set forth above. A first therapy (e.g., a prophylactic or therapeutic agent such as a compound provided herein, a compound provided herein, e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy (e.g., administration of three active compositions) is also contemplated herein.

Administration of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be independent of the route of administration of a second therapy. In one embodiment, Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is administered orally. In another embodiment, Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is administered intravenously. Thus, in accordance with these embodiments, Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof and a second therapy are administered by the same mode of administration, orally or by IV. In another embodiment, Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is administered by one mode of administration, e.g., by orally, whereas the second agent (an anticancer agent) is administered by another mode of administration, e.g., IV.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein and any optional additional active agents concurrently administered to the patient.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 mcg (in smaller patients) or 480 mcg subcutaneously. In certain embodiments, EPO may be administered subcutaneously in an amount of 10,000 Unit 3 times per week.

Compound A or an enantiomer or a mixture of enantiomers thereof, a pharmaceutically acceptable stereoisomer, a pharmaceutically acceptable salt, prodrug, solvate, hydrate, co-crystal, clathrate, or polymorph thereof can be co-administered with secondary agents described herein to treat, prevent, or manage cancer.

In one embodiment, a compound provided herein, e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered in an effective amount in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, e.g., Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered in an effective amount to patients with diseases and disorders associated with or characterized by, undesired angiogenesis in combination with additional active ingredients, including, but not limited to, anti-cancer drugs.

Also provided herein is a method of treating, preventing or managing cancer by administering Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein, in combination with (e.g., before, during, or after) conventional therapy including, but not limited to, surgery, immunotherapy, biological therapy, radiation therapy, or other non-drug based therapy used to treat, prevent or manage cancer. The combined use of the compound in a dosage form described herein and conventional therapy may provide a unique treatment regimen that is unexpectedly effective in certain patients. Without being limited by theory, it is believed that Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof may provide additive or synergistic effects when given concurrently with conventional therapy.

As discussed elsewhere herein, included herein are methods of reducing, treating or preventing adverse or undesired effects associated with conventional therapy including, but not limited to, surgery, chemotherapy, radiation therapy, hormonal therapy, biological therapy and immunotherapy by administering Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein and one or more other active ingredients can be administered to a patient prior to, during, or after the occurrence of the adverse effect associated with conventional therapy.

In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein can be administered in an amount ranging from about 0.1 to about 150 mg, from about 1 to about 25 mg, or from about 2 to about 10 mg, in a dosage form described herein, orally and daily alone, or in combination with a second active agent, prior to, during, or after the use of conventional therapy.

As those of ordinary skill in the art are aware, the treatment of cancer is often based on the stages and mechanism of the disease. For example, if leukemic transformation develops in certain stages of cancer, transplantation of peripheral blood stem cells, hematopoietic stem cell preparation or bone marrow may be necessary. The combined use of Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein and transplantation therapy provides a unique and unexpected synergism. In particular, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein exhibits immunomodulatory activity that may provide additive or synergistic effects when given concurrently with transplantation therapy in patients with cancer.

Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein can work in combination with transplantation therapy thereby reducing complications associated with the invasive procedure of transplantation and risk of GVHD. Thus, included herein are methods of treating, preventing or managing cancer by administering to a patient (e.g., a human) Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein, before, during, or after the transplantation of umbilical cord blood, placental blood, peripheral blood stem cell, hematopoietic stem cell preparation to a patient in need thereof. Some examples of stem cells suitable for use in the methods provided herein are disclosed in U.S. Pat. No. 7,498,171, the disclosure of which is incorporated herein by reference in its entirety.

In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered to patients with multiple myeloma before, during, or after the transplantation of autologous peripheral blood progenitor cell to treat multiple myeloma.

In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered to patients with relapsing multiple myeloma after the stem cell transplantation to treat multiple myeloma.

In yet another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein and prednisone are administered as maintenance therapy to patients with multiple myeloma following the transplantation of autologous stem cell.

In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered to patients with NHL (e.g., DLBCL) before, during, or after the transplantation of autologous peripheral blood progenitor cell.

In another embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered to patients with NHL (e.g., DLBCL) after stem cell transplantation.

In one embodiment, Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof, in a dosage form described herein is administered daily and continuously for three or four weeks at a dose of from about 0.1 to about 150 mg/d followed by a break of one or two weeks.

Embodiments provided herein may be more fully understood by reference to the following examples. These examples are meant to be illustrative of pharmaceutical compositions and dosage forms provided herein, but are not in any way limiting

6. Examples

Formulations of Compound A as described herein were studied with the absence of Anhydrous Lactose and the replacement of Magnesium Stearate with Stearic Acid, as well as the feasibility of encapsulating on the Bosch GKF 700L Capsule Filler.

Formulations of Compound A as Capsules were manufactured at 1, 2, 3, 4, and 5 mg strengths. The manufacturing process included two separate campaigns of R&D engineering batch records, consisting of six batch records in the first campaign, and eight batch records in the second campaign. The first campaign used fillers other than Anhydrous Lactose while the second campaign used fillers other than Anhydrous Lactose and an lubricants other than Magnesium Stearate. The inventors discovered, inter alia, that the presence of lactose in formulations with the active compound appears to cause degradation and instability of the dosage form. The inventors also discovered, inter alia, that croscarmellose sodium and magnesium stearate also appear to cause degradation and instability of the dosage form. Each record included dry blending and encapsulation as described herein. Sampling protocols were also executed as part of each record to collect additional in-process data.

Table 1 provides a summary of the manufactured batches to support the evaluation of the formulations along with the batches manufactured for the B130491 control formulation. Table 2 lists the formula used in the R&D engineering batches. A process flow diagram is provided in FIG. 1. Tables 6 and 7 list exemplary dosage form formulations at 1 mg and 3 mg strengths of Compound respectively. Table 8 lists exemplary dosage form formulations for 1, 2, 3, 4, and 5 mg strengths of Compound A.

6.1 Blending

Blending took place in an 8 Qt. V-blender. All excipients, except magnesium stearate or stearic acid, were de-lumped through a Comil 197S equipped with a round impeller (1601) and a dedicated screen (2A032R02528). The Compound A container was rinsed with a portion of de-lumped Prosolv SMCC 50 for formulations F1 and F3, Starch 1500 for formulations F2 and F7, or Microcrystalline Cellulose (Type PH-102) for formulations F4, F5, and F6. The rinsate was then charged to the blender. After the initial blend, the material was discharged and passed through the Comil to further disperse the ingredients. Table 3 summarizes the blending process parameters for each R&D batch.

Samples of the final blend were pulled for bulk and tapped density, flow (Flodex), and particle size testing. Blend uniformity samples were also pulled from the final blend and only tested if needed for each batch. The blend uniformity of samples for batch RD14064 were tested. The results are listed below in Table 4.

Table 5 summarizes the final blend physical characteristics and compares the data to data collected for the B130491 control formulation. FIG. 2A and FIG. 2B summarize the particle size distribution.

The blend uniformity results for RD14064 suggests that the blend is uniform as indicated by the low % RSD. The low assay results are not attributed to processing or handling, as the manufacturing for all 14 batches are the same, aside from changes with filler and lubricants.

The differences in the particle distribution are attributed to the change in fillers (lactose, Prosolv SMCC 50, mannitol, starch 1500, and Microcrystalline Cellulose (Type PH-102)). The B130491 control formulation contains the most fines with lactose.

TABLE 1

Batch Summary

| Batch # | Title | Batch Size |
|---|---|---|
| B130491 | Compound A, 1 mg Capsules (Equivalent to 1.127 mg HCl Salt), 3.686 kg | 3.686 kg (36,860 Capsules) |
| B130458 | Compound A, 3 mg Capsules (Equivalent to 3.38 mg HCl Salt), 3.686 kg | 3.686 kg (30,716 Capsules) |
| RD14022 | Compound A, 1 mg Capsules (F-1 Formulation), 1.788 kg | 1.788 kg (17,880 Capsules) |
| RD14023 | Compound A, 1 mg Capsules (F-2 Formulation), 1.788 kg | 1.788 kg (17,880 Capsules) |
| RD14024 | Compound A, 1 mg Capsules (F-3 Formulation), 1.788 kg | 1.788 kg (17,880 Capsules) |
| RD14025 | Compound A, 3 mg Capsules (F-1 Formulation), 1.788 kg | 1.788 kg (14,900 Capsules) |
| RD14026 | Compound A, 3 mg Capsules (F-2 Formulation), 1.788 kg | 1.788 kg (14,900 Capsules) |
| RD14027 | Compound A, 3 mg Capsules (F-3 Formulation), 1.788 kg | 1.788 kg (14,900 Capsules) |
| RD14059 | Compound A, 3 mg Capsules (F-4 Formulation), 1.788 kg | 1.788 kg (14,900 Capsules) |
| RD14060 | Compound A, 3 mg Capsules (F-5 Formulation), 1.788 kg | 1.788 kg (14,900 Capsules) |
| RD14061 | Compound A, 3 mg Capsules (F-6 Formulation), 1.788 kg | 1.788 kg (14,900 Capsules) |
| RD14062 | Compound A, 1 mg Capsules (F-4 Formulation), 1.788 kg | 1.788 kg (17,880 Capsules) |
| RD14063 | Compound A, 1 mg Capsules (F-5 Formulation), 1.788 kg | 1.788 kg (17,880 Capsules) |
| RD14064 | Compound A, 1 mg Capsules (F-6 Formulation), 1.788 kg | 1.788 kg (17,880 Capsules) |
| RD14070 | Compound A, 1 mg Capsules (F-7 Formulation), 1.788 kg | 1.788 kg (17,880 Capsules) |
| RD14071 | Compound A, 3 mg Capsules (F-7 Formulation), 1.788 kg | 1.788 kg (14,900 Capsules) |

TABLE 2

Theoretical Unit Formula for Compound A Capsules

| Ingredient | Material Number | B130491 (Control) | RD14022 (F1) | RD14023 (F2) | RD14024 (F3) | RD14062 (F4) | RD14063 (F5) | RD14064 (F6) | RD14070 (F7) |
|---|---|---|---|---|---|---|---|---|---|
| | | Concentration (mg/capsule) | | | | | | | |
| Compound A HCl | RM3562 | | | | 1.13 [1] | | | | |
| Silicified Microcrystalline Cellulose (Prosolv SMCC 50) | RM3219 | 69.37 | 69.37 | — | 73.37 | — | — | — | — |
| Microcrystalline Cellulose (Type PH-102) | RM00094 | — | — | — | — | 55.70 | 55.70 | 51.70 | — |

TABLE 2-continued

Theoretical Unit Formula for Compound A Capsules

| Ingredient | Material Number | | | | | | | | |
|---|---|---|---|---|---|---|---|---|---|
| Anhydrous Lactose (Lactopress ® Anhydrous Fine Powder) Product Code: 585555 | RM3569 | 24.75 | — | — | — | — | — | — | — |
| Pregelatinized Starch | RM00087 | — | — | 68.37 | — | — | — | — | 51.70 |
| Mannitol (Mannogem EZ Spray Dried) | RM2835 | — | 24.75 | 24.75 | 24.75 | 41.42 | 41.42 | 41.42 | 41.42 |
| Crospovidone (Kollidon ® CL) Type A | RM3189 | — | — | — | — | — | — | 4.00 | 4.00 |
| Aerosil ® 200 (Colloidal Silicon Dioxide) | RM01175 | — | — | 1.00 | — | 1.00 | 1.00 | 1.00 | 1.00 |
| Croscarmellose Sodium | RM00079 | 4.00 | 4.00 | 4.00 | — | — | — | — | — |
| Stearic Acid (Hystrene) 5016 Vegetable Powder | RM2813 | — | — | — | — | 0.75 | — | 0.75 | 0.75 |
| Magnesium Stearate (HyQual ®), Vegetable Source Product Code 2257 Vendor Identification: Kosher Passover HyQual | RM2846 | 0.75 | 0.75 | 0.75 | 0.75 | — | 0.75 | — | — |
| Total amount per capsule: | | 100.00 | 100.00 | 100.00 | 100.00 | 100.00 | 100.00 | 100.00 | 100.00 |
| Capsule: Size 3 Bovine Swedish Orange (9209) Opaque Capsule Shell (CONI-SNAP) Part # G3ICS001009 | RM3594 | 1 ea | 1 ea | 1 ea | 1 ea | 1 ea | 1 ea | 1 ea | 1 ea |

| Ingredient | Material Number | B130458 (Original) | RD14025 (F1) | RD14026 (F2) | RD14027 (F3) | RD14059 (F4) | RD14060 (F5) | RD14061 (F6) | RD14071 (F7) |
|---|---|---|---|---|---|---|---|---|---|
| | | Concentration (mg/capsule) | | | | | | | |
| Compound A HCl | RM3562 | | | | 3.38 [1] | | | | |
| Silicified Microcrystalline Cellulose (Prosolv SMCC 50) | RM3219 | 81.22 | 81.22 | — | 86.02 | — | — | — | — |
| Microcrystalline Cellulose (Type PH-102) | RM00094 | — | — | — | — | 64.82 | 64.82 | 60.02 | — |
| Anhydrous Lactose (Lactopress ® Anhydrous Fine Powder) Product Code: 585555 | RM3569 | 29.70 | — | — | — | — | — | — | — |
| Pregelatinized Starch | RM00087 | — | — | 80.02 | — | — | — | — | 60.02 |
| Mannitol (Mannogem EZ Spray Dried) | RM2835 | — | 29.70 | 29.70 | 29.70 | 49.70 | 49.70 | 49.70 | 49.70 |
| Crospovidone (Kollidon ® CL) Type A | RM3189 | — | — | — | — | — | — | 4.80 | 4.80 |
| Aerosil ® 200 (Colloidal Silicon Dioxide) | RM01175 | — | — | 1.20 | — | 1.20 | 1.20 | 1.20 | 1.20 |

TABLE 2-continued

Theoretical Unit Formula for Compound A Capsules

| | | | | | | | | | |
|---|---|---|---|---|---|---|---|---|---|
| Croscarmellose Sodium | RM00079 | 4.80 | 4.80 | 4.80 | — | — | — | — | — |
| Stearic Acid (Hystrene) 5016 Vegetable Powder | RM2813 | — | — | — | — | 0.90 | — | 0.90 | 0.90 |
| Magnesium Stearate (HyQual ®), Vegetable Source Product Code 2257 Vendor Identification: Kosher Passover HyQual | RM2846 | 0.90 | 0.90 | 0.90 | 0.90 | — | 0.90 | — | — |
| Total amount per capsule: | | 120.00 | 120.00 | 120.00 | 120.00 | 120.00 | 120.00 | 120.00 | 120.00 |
| Capsule: Size 3 Bovine Swedish Orange (9209) Opaque Capsule Shell (CONI-SNAP) Part # G3ICS001009 | RM3594 | 1 ea | 1 ea | 1 ea | 1 ea | 1 ea | 1 ea | 1 ea | 1 ea |

[1] Based on Compound A base (1.13 mg and 3.38 mg of Compound A HCL is equivalent to 1.00 mg and 3.00 mg base, respectively)

TABLE 3

Blending Parameters for Blend Preparation

| Parameter | RD14022 (F1) | RD14023 (F2) | RD14024 (F3) | RD14062 (F4) | RD14063 (F5) | RD14064 (F6) | RD14070 (F7) |
|---|---|---|---|---|---|---|---|
| | | | | 1 mg strength | | | |
| Blender Size & Type | | | | 8 Qt V-Blender | | | |
| SUPAC Designation (Class; Sub-class) | | | Diffusion Mixer (Tumble); V-Blender | | | | |
| Target Working Volume (L) | | | | 7.6 | | | |
| Total Volume (L) | | | | 11.7 | | | |
| Working Volume Fill Ratio % | 60 | 40 | 61 | 56 | 56 | 55 | 40 |
| Total Volume Fill Ratio (%) | 39 | 26 | 39 | 36 | 36 | 36 | 26 |
| Pre-Blend Number of Revolutions (~time: min) [1] | | | | 150 (~6 min) | | | |
| Blend Number of Revolutions (~time: min) [1] | | | | 360 (~14 min) | | | |
| Lubrication Number of Revolutions (~time: min) [1] | | | | 45 (~2 min) | | | |

| Parameter | RD14025 (F1) | RD14026 (F2) | RD14027 (F3) | RD14059 (F4) | RD14060 (F5) | RD14061 (F6) | RD14071 (F7) |
|---|---|---|---|---|---|---|---|
| | | | | 3 mg strength | | | |
| Blender Size & Type | | | | 8 Qt V-Blender | | | |
| SUPAC Designation (Class; Sub-class) | | | Diffusion Mixer (Tumble); V-Blender | | | | |
| Target Working Volume (L) | | | | 7.6 | | | |
| Total Volume (L) | | | | 11.7 | | | |
| Working Volume Fill Ratio % | 59 | 42 | 60 | 55 | 56 | 56 | 40 |
| Total Volume Fill Ratio (%) | 38 | 27 | 39 | 36 | 37 | 36 | 26 |

TABLE 3-continued

Blending Parameters for Blend Preparation

| | |
|---|---|
| Pre-Blend Number of Revolutions (~time: min) [1] | 150 (~6 min) |
| Blend Number of Revolutions (~time: min) [1] | 360 (~14 min) |
| Lubrication Number of Revolutions (~time: min) [1] | 45 (~2 min) |

[1] EQ #125 does not have a counter, only a timer

TABLE 4

Compound Dosage form Critical Quality Attributes

| | | Content Uniformity | |
|---|---|---|---|
| Strength | % RSD | Assay | AV |
| 0.5 mg | 1.6 | 102.3 | 4.7 |
| 1 mg | 1.6 | 102.3 | 4.7 |
| 2 mg | 1.8 | 100.6 | 4.5 |
| 3 mg | 1.9 | 99.5 | 4.5 |
| 3.5 mg | 1.6 | 101.0 | 3.3 |
| 4 mg | 1.8 | 100.7 | 4.4 |
| 5 mg | 1.1 | 99.3 | 2.7 |

TABLE 6

Exemplary Formulations of 1 mg Compound A

| | mg/capsule | |
|---|---|---|
| Formulation Components | F-4 | F-6 |
| Compound A | 1.127 | 1.127 |
| Avicel PH 102 | 55.703 | 51.703 |
| Spray dried mannitol | 41.42 | 41.42 |
| Crospovidone | — | 4 |
| Aerosil | 1 | 1 |

TABLE 5

Final Blend Physical Results for Formulations Herein

| Parameter | | B130491 (Control) | RD14022 (F1) | RD14023 (F2) | RD14024 (F3) | RD14062 (F4) | RD14063 (F5) | RD14064 (F6) | RD14070 (F7) |
|---|---|---|---|---|---|---|---|---|---|
| | | | | | | 1 mg strength | | | |
| Bulk Density (g/mL) | | 0.38 | 0.39 | 0.59 | 0.39 | 0.42 | 0.42 | 0.43 | 0.58 |
| Tapped Density (g/mL) | | 0.55 | 0.52 | 0.83 | 0.51 | 0.54 | 0.55 | 0.54 | 0.77 |
| Critical Orifice (mm) | | 26 | 8 | 16 | 10 | 4 | 5 | 4 | 12 |
| Particle Size | Sieve # (μm) | | | | | | | | |
| by Sieve | 60 (250) | 1.07% | 0.79% | 1.48% | 0.88% | 0.7% | 0.6% | 1.6% | 1.4% |
| (% retained) | 80 (180) | 0.78% | 4.25% | 8.60% | 4.51% | 13.7% | 13.4% | 14.1% | 8.6% |
| | 100 (150) | 0.49% | 5.73% | 6.82% | 5.48% | 10.4% | 10.3% | 15.0% | 11.1% |
| | 140 (106) | 4.77% | 14.33% | 17.19% | 14.01% | 34.1% | 33.7% | 28.2% | 22.9% |
| | 200 (75) | 17.92% | 17.89% | 19.96% | 22.14% | 14.9% | 16.9% | 15.9% | 14.3% |
| | 325 (45) | 20.64% | 30.34% | 27.27% | 31.73% | 14.8% | 15.6% | 14.8% | 17.3% |
| | Pan (<45) | 54.33% | 26.68% | 18.68% | 21.25% | 11.4% | 9.5% | 10.4% | 24.4% |

| Parameter | | B130458 (Original) | RD14025 (F1) | RD14026 (F2) | RD14027 (F3) | RD14059 (F4) | RD14060 (F5) | RD14061 (F6) | RD14071 (F7) |
|---|---|---|---|---|---|---|---|---|---|
| | | | | | | 3 mg strength | | | |
| Bulk Density (g/mL) | | 0.38 | 0.40 | 0.56 | 0.40 | 0.43 | 0.42 | 0.42 | 0.58 |
| Tapped Density (g/mL) | | 0.56 | 0.52 | 0.81 | 0.51 | 0.53 | 0.53 | 0.54 | 0.76 |
| Critical Orifice (mm) | | 28 | 9 | 16 | 14 | 6 | 12 | 8 | 16 |
| Particle Size | Sieve # (μm) | | | | | | | | |
| by Sieve | 60 (250) | 0.78% | 0.78% | 1.16% | 0.68% | 1.1% | 1.7% | 1.6% | 1.1% |
| (% retained) | 80 (180) | 0.68% | 4.57% | 7.86% | 6.26% | 13.2% | 12.5% | 15.2% | 8.1% |
| | 100 (150) | 0.59% | 6.32% | 11.06% | 7.44% | 16.3% | 15.0% | 16.2% | 11.0% |
| | 140 (106) | 7.23% | 15.08% | 17.75% | 15.85% | 26.1% | 27.7% | 25.3% | 23.9% |
| | 200 (75) | 20.70% | 18.48% | 20.47% | 20.55% | 16.2% | 15.6% | 15.0% | 14.3% |
| | 325 (45) | 17.29% | 29.09% | 17.85% | 29.55% | 16.0% | 15.8% | 15.1% | 17.8% |
| | Pan (<45) | 52.73% | 25.68% | 23.86% | 19.67% | 11.2% | 11.6% | 11.7% | 23.8% |

TABLE 6-continued

Exemplary Formulations of 1 mg Compound A

| Formulation Components | mg/capsule | |
| --- | --- | --- |
| | F-4 | F-6 |
| Stearic acid | 0.75 | 0.75 |
| Gelatin capsule size | 3 | 3 |
| Total fill weight per capsule (mg) | 100 | 100 |

TABLE 7

Exemplary Formulations of 3 mg Compound A

| Formulation Components | mg/capsule | |
| --- | --- | --- |
| | F-4 | F-6 |
| Compound A | 3.381 | 3.381 |
| Avicel PH 102 | 64.819 | 60.019 |
| Spray dried mannitol | 49.7 | 49.7 |
| Crospovidone | — | 4.8 |
| Aerosil | 1.2 | 1.2 |
| Stearic acid | 0.9 | 0.9 |
| Gelatin capsule size | 3 | 3 |
| Total fill weight per capsule (mg) | 120 | 120 |

TABLE 8

Exemplary Formulations of 1, 2, 3, 4, and 5 mg strength dosage forms of Compound A

| Formulation Components | Compound capsules (mg/capsule) | | | | | | |
| --- | --- | --- | --- | --- | --- | --- | --- |
| | 0.5 mg | 1 mg | 2 mg | 3 mg | 3.5 mg | 4 mg | 5 mg |
| Compound A (HCl salt) | 0.564 | 1.127 | 2.254 | 3.381 | 3.945 | 4.508 | 5.635 |
| Microcrystalline Cellulose (Avicel PH 102) | 52.267 | 51.703 | 103.406 | 60.019 | 70.022 | 80.025 | 100.031 |
| Spray dried mannitol (Mannogem EZ) | 41.42 | 41.42 | 82.84 | 49.70 | 57.983 | 66.267 | 82.834 |
| Crospovidone (Kollidon CL Type A) | 4.00 | 4 | 8 | 4.8 | 5.6 | 6.4 | 8.0 |
| Colloidal Silicon Dioxide (Aerosil 200) | 1.00 | 1 | 2 | 1.2 | 1.4 | 1.6 | 2.0 |
| Stearic acid (Hystrene) | 0.75 | 0.75 | 1.50 | 0.9 | 1.05 | 1.2 | 1.5 |
| Gelatin capsule size (Pinkish Brown) | 3 | 3 | 1 | 3 | 2 | 2 | 1 |
| Total fill weight per capsule (mg) | 100 | 100 | 200 | 120 | 140 | 160 | 200 |

6.2 Encapsulation

Table 9 summarizes the encapsulation process parameters for each R&D batch and compares it to batches of the control formulation (B130491 and B130458). Batches RD14023, RD14026, RD14070, and RD14071 did not form slugs upon tamping and utilized a flood filling process.

The in-process data collected during encapsulation is summarized in Table 10.

The data for all batches indicates the capsules were within the specification limits presented in Table 10. The CpK values are based on 3-sigma variation from the mean and show how well the data is centered between the specification limits. A CpK value of 1.33 indicates the process is capable of controlling variation to 4-sigma from the mean. The CpK values for batches RD14064, RD14060, and RD14071 indicate that the process is capable of controlling variation to 3-sigma from the mean. The CpK value for batch RD14070 indicates that the process is not capable of controlling variation. The CpK equation is shown below.

$$CpK = \min\left(\frac{USL - \text{Average}}{3\sigma}, \frac{\text{Average} - LSL}{3\sigma}\right)$$ CpK Equation A composite sample was collected and tested for content uniformity. A graphical display of the bulk product content uniformity test results for the original and alternative formulations are presented in FIG. 3A and FIG. 3B. All samples met the requirements of cUSP <905> and suggest Compound A maintains homogeneity during gross handling of the bulk blend and compression with low AV.

No correlation can be made to particle size distribution and CpK or bulk and tapped density and CpK. Table 7 indicates that all batch data (except RD14064, RD14070, RD14060, and RD14071) fell within the specification limits and meet tighter in-process control limits for weight. The data indicate operating the Bosch GKF 700L ~90 upm is suitable to successfully manufacture capsules meeting all in-process controls. The data collected to date suggest that the API drug load concentration along with processing times impact content uniformity less for the 3 mg strength compared to the 1 mg strength.

Replacing Anhydrous Lactose with Silicified Microcrystalline Cellulose, Mannitol, Starch 1500, or Microcrystalline Cellulose (Type PH-102) has little impact on process control and content uniformity.

Clinical batches are being manufactured utilizing formulations F4 and F6 (Table 6 and Table 7). A 12 mm size 4 dosing disk was used during the manufacture of formulation F6 at the 1 mg strength due to the low fill weights observed during manufacture of batch RD14064.

Both F4 and F6 formulation showed similar performance with regards to stability, manufacturability and PK parameters. Stability data from 6-month time point showed significant improvement on product performance (dissolution of capsules) of Formulation F4 (data not shown) and Formulation F6 (FIG. 5A, FIG. 5B, FIG. 6A, and FIG. 6B) as compared to the formulation that contains lactose, croscarmellose sodium, and magnesium stearate (FIG. 4A and FIG. 4B).

While examples of certain particular embodiments are provided herein, it will be apparent to those skilled in the art that various changes and modifications may be made. Such modifications are also intended to fall within the scope of the appended claims.

TABLE 9

Bosch 700 L Setup Parameters

| Parameter | | B130491 (Control) | RD14022 (F1) | RD14023 (F2) | RD14024 (F3) | RD14062 (F4) | RD14063 (F5) | RD14064 (F6) | RD14070 (F7) |
|---|---|---|---|---|---|---|---|---|---|
| | | | | | 1 mg strength | | | | |
| Dosing Disk | | 4 | 4 | 4 | 4 | 4 | 4 | 4 | 4 |
| Dosing Disk Size (mm) | | 10 | 10 | 8 | 10 | 10 | 10 | 10 | 8 |
| Machine Speed (upm) | | 100 | 98 | 98 | 98 | 90 | 90 | 90 | 90 |
| Powder Bed Height (mm) | | 20 | 25 | 30 | 25 | 20 | 20 | 20 | 30 |
| Tamping | 1 | 7 | 8 | 6 | 8 | 8 | 8 | 8 | 6 |
| Pin Setting | 2 | 6 | 8 | 6 | 8 | 8 | 8 | 8 | 4 |
| | 3 | 6 | 7 | 6 | 7 | 7 | 7 | 7 | 3 |
| | 4 | 7 | 7 | 6 | 7 | 7 | 7 | 6 | 3 |
| | 5 | 10 | 7 | 6 | 7 | 7 | 7 | 6 | 3 |

| Parameter | | B130458 (Control) | RD14025 (F1) | RD14026 (F2) | RD14027 (F3) | RD14059 (F4) | RD14060 (F5) | RD14061 (F6) | RD14071 (F7) |
|---|---|---|---|---|---|---|---|---|---|
| | | | | | 3 mg strength | | | | |
| Dosing Disk | | 3 | 3 | 4 | 3 | 4 | 4 | 3 | 4 |
| Dosing Disk Size (mm) | | 10 | 10 | 10 | 10 | 10 | 10 | 10 | 10 |
| Machine Speed (upm) | | 100 | 98 | 98 | 98 | 90 | 90 | 90 | 90 |
| Powder Bed Height (mm) | | 20 | 25 | 25 | 25 | 20 | 20 | 20 | 30 |
| Tamping | 1 | 6 | 10 | 10 | 10 | 10 | 10 | 10 | 8 |
| Pin Setting | 2 | 8 | 10 | 10 | 10 | 10 | 10 | 10 | 8 |
| | 3 | 8 | 8 | 10 | 8 | 10 | 10 | 7 | 7 |
| | 4 | 10 | 7 | 15 | 7 | 9 | 8 | 5 | 7 |
| | 5 | 10 | 6 | 9 | 6 | 7 | 8 | 5 | 7 |

TABLE 10

Encapsulation - In-Process Data

| Batch # | Target (mg) | Lower Spec Limit (mg) | Upper Spec Limit (mg) | Min (mg) | Max (mg) | Range (mg) | Count | Average (mg) | % RSD | CpK |
|---|---|---|---|---|---|---|---|---|---|---|
| | | | | 1 mg Strength | | | | | | |
| B130491 (Control) | 148 | 138 | 158 | 145 | 155 | 10 | 90 | 150 | 1.21 | 1.39 |
| RD14022 (F1) | 148 | 138 | 158 | 146 | 150 | 4 | 60 | 148 | 0.71 | 3.14 |
| RD14023 (F2) | 147 | 137 | 157 | 142 | 148 | 6 | 50 | 146 | 0.94 | 2.08 |
| RD14024 (F3) | 148 | 138 | 158 | 146 | 151 | 5 | 60 | 148 | 0.76 | 2.88 |
| RD14062 (F4) | 147 | 137 | 157 | 143 | 152 | 9 | 70 | 148 | 1.34 | 1.57 |
| RD14063 (F5) | 147 | 137 | 157 | 143 | 152 | 9 | 70 | 148 | 1.34 | 1.58 |
| RD14064 (F6) | 147 | 137 | 157 | 139 | 149 | 10 | 80 | 145 | 1.53 | 1.17 |
| RD14070 (F7) | 147 | 137 | 157 | 140 | 155 | 15 | 60 | 145 | 2.30 | 0.82 |
| | | | | 3 mg Strength | | | | | | |
| B130458 (Control) | 168 | 156 | 180 | 163 | 170 | 7 | 65 | 167 | 0.98 | 2.30 |
| RD14025 (F1) | 168 | 156 | 180 | 163 | 172 | 9 | 50 | 168 | 1.26 | 1.85 |
| RD14026 (F2) | 168 | 156 | 180 | 167 | 172 | 5 | 40 | 169 | 0.72 | 2.96 |
| RD14027 (F3) | 168 | 156 | 180 | 165 | 172 | 7 | 50 | 168 | 1.21 | 1.94 |
| RD14059 (F4) | 167 | 155 | 179 | 160 | 174 | 14 | 60 | 166 | 1.67 | 1.37 |
| RD14060 (F5) | 167 | 155 | 179 | 162 | 175 | 13 | 60 | 168 | 1.62 | 1.29 |
| RD14061 (F6) | 167 | 155 | 179 | 161 | 170 | 9 | 60 | 167 | 1.14 | 2.09 |
| RD14071 (F7) | 167 | 155 | 179 | 158 | 169 | 11 | 60 | 164 | 1.45 | 1.31 |

What is claimed:

1. An oral dosage form in the form of a capsule, said dosage form comprising a composition, wherein the composition comprises: Compound A (3-(5-amino-2-methyl-4-oxo-4H-quinazolin-3-yl)-piperidine-2,6-dione), or an enantiomer or a mixture of enantiomers thereof, a pharmaceutically acceptable salt, solvate, hydrate, co-crystal, clathrate, or polymorph thereof, at an amount of about 0.5 to about 5 weight percent of the total weight of the composition; a binder or filler selected from microcrystalline cellulose, starch, and mannitol at an amount of about 90 to 98 weight percent of total weight of the composition, stearic acid in an amount of about 0 to 2 weight percent of total weight of the composition, and a disintegrant selected from crospovidone Type A and colloidal silicon dioxide at an amount of about 1 to 5 weight percent of total weight of the composition.

2. The oral dosage form of claim 1, wherein said lubricant is present at an amount of about 0.75 weight percent of total weight of the composition.

3. The oral dosage form of claim 1, wherein the microcrystalline cellulose is low moisture grade microcrystalline cellulose.

4. The oral dosage form of claim 1, wherein the mannitol is spray dried mannitol.

5. The oral dosage form of claim 1, wherein Compound A, or an enantiomer or a mixture of enantiomers thereof, a pharmaceutically acceptable stereoisomer, a pharmaceutically acceptable salt, prodrug, solvate, hydrate, co-crystal, clathrate, or polymorph thereof is present at an amount that provides about 0.5, 1, 2, 3, 3.5, 4, or 5 mg Compound A.

6. The oral dosage form of claim 1, comprising HCl salt of Compound A.

7. An oral dosage form, said oral dosage form comprising a composition, wherein the composition comprises: Compound A (3-(5-amino-2-methyl-4-oxo-4H-quinazolin-3-yl)-piperidine-2,6-dione), or an enantiomer or a mixture of enantiomers thereof, a pharmaceutically acceptable salt, solvate, hydrate, co-crystal, clathrate, or polymorph thereof, at an amount that provides 0.5, 1, 2, 3, 3.5, 4, or 5 mg Compound A; and a pharmaceutically acceptable carrier or excipient wherein said pharmaceutically acceptable carrier or excipient comprises a binder or filler selected from microcrystalline cellulose, starch, and mannitol at an amount of about 90 to 98 weight percent of total weight of the composition, stearic acid in an amount of about 0 to 2 weight percent of total weight of the composition, and a disintegrant selected from crospovidone Type A and colloidal silicon dioxide at an amount of about 1 to 5 weight percent of total weight of the composition.

8. The oral dosage form of claim 7, wherein said cellulose is microcrystalline cellulose.

9. The oral dosage form of claim 8, wherein said microcrystalline cellulose is low moisture grade microcrystalline cellulose.

10. The oral dosage form of claim 7, wherein said mannitol is spray dried mannitol.

11. The oral dosage form of claim 7, wherein said disintegrant is crospovidone Type A or colloidal silicon dioxide.

12. The oral dosage form of claim 7, comprising HCl salt of Compound A.

13. The oral dosage form of claim 7, which weighs about 100 mg and provides 1 mg Compound A.

14. The oral dosage form of claim 7, which weighs about 120 mg and provides 3 mg Compound A.

15. The oral dosage form of claim 7, which weighs about 200 mg and provides 2 mg Compound A.

16. The oral dosage form of claim 7, which weighs about 100 mg and provides 0.5 mg Compound A.

17. The oral dosage form of claim 7, which weighs about 140 mg and provides 3.5 mg Compound A.

18. The oral dosage form of claim 7, which weighs about 160 mg and provides 4 mg Compound A.

19. The oral dosage form of claim 7, which weighs about 200 mg and provides 5 mg Compound A.

20. A method for treating, preventing, or managing cancer, said method comprising administering to a patient an oral dosage form of claim 1.

21. A method for treating, preventing, or managing cancer, said method comprising administering to a patient an oral dosage form of claim 7.

* * * * *